(12) United States Patent
Nozaki

(10) Patent No.: US 10,390,708 B2
(45) Date of Patent: Aug. 27, 2019

(54) OPTICAL MEASURING DEVICE AND TOOTHBRUSH PROVIDED WITH SAME

(71) Applicant: CITIZEN WATCH CO., LTD., Tokyo (JP)

(72) Inventor: Takaaki Nozaki, Saitama (JP)

(73) Assignee: CITIZEN WATCH CO., LTD., Tokyo (JP)

( * ) Notice: Subject to any disclaimer, the term of this patent is extended or adjusted under 35 U.S.C. 154(b) by 0 days.

(21) Appl. No.: 15/555,405

(22) PCT Filed: Feb. 29, 2016

(86) PCT No.: PCT/JP2016/056112
§ 371 (c)(1),
(2) Date: Sep. 1, 2017

(87) PCT Pub. No.: WO2016/140199
PCT Pub. Date: Sep. 9, 2016

(65) Prior Publication Data
US 2018/0035896 A1    Feb. 8, 2018

(30) Foreign Application Priority Data
Mar. 2, 2015 (JP) .................. 2015-040228

(51) Int. Cl.
*A61B 5/00* (2006.01)
*A46B 9/04* (2006.01)
(Continued)

(52) U.S. Cl.
CPC .............. *A61B 5/0088* (2013.01); *A46B 9/04* (2013.01); *A46B 15/0036* (2013.01); *A61B 1/00* (2013.01);
(Continued)

(58) Field of Classification Search
CPC .............. A61B 5/0088; A46B 15/0036; A46B 2200/1066; A61C 17/221; G01N 21/64
(Continued)

(56) References Cited

U.S. PATENT DOCUMENTS

| 5,306,144 A | 4/1994 | Hibst et al. |
| 6,485,300 B1 | 11/2002 | Muller et al. |

(Continued)

FOREIGN PATENT DOCUMENTS

| JP | H06-073531 B2 | 9/1994 |
| JP | 2002-515726 A | 5/2002 |

(Continued)

OTHER PUBLICATIONS

International Search Report for PCT/JP2016/056112, dated May 24, 2016.

(Continued)

*Primary Examiner* — Matthew M Nelson

(57) ABSTRACT

Provided is an optical measuring device that can properly detect a small amount of dental plaque, can be easily incorporated into a toothbrush, and has a simple configuration. The optical measuring device includes a plurality of light sources that irradiate a sample with light having a plurality of wavelengths different from each other, respectively, a detection unit that detects intensities of examined light generated when the sample is irradiated with the light having the plurality of wavelengths, and a control unit that calculates an amount of fluorescent substance to be measured, based on the intensities of the examined light detected by the detection unit in response to the light having the plurality of wavelengths.

14 Claims, 11 Drawing Sheets

(51) Int. Cl.
    *A61B 1/00*     (2006.01)
    *A61B 1/24*     (2006.01)
    *G01N 21/64*     (2006.01)
    *A46B 15/00*     (2006.01)
    *A61C 17/22*     (2006.01)

(52) U.S. Cl.
    CPC .............. *A61B 1/24* (2013.01); *A61C 17/221* (2013.01); *G01N 21/64* (2013.01); *A46B 2200/1066* (2013.01)

(58) Field of Classification Search
    USPC .......................................................... 433/29
    See application file for complete search history.

(56) References Cited

U.S. PATENT DOCUMENTS

| | | | | |
|---|---|---|---|---|
| 2003/0156788 A1* | 8/2003 | Henning | ............... | A61B 5/0088 385/31 |
| 2007/0105069 A1* | 5/2007 | Yamagishi | ........... | A61B 5/0088 433/215 |
| 2011/0151409 A1* | 6/2011 | Binner | ................. | A61B 1/0646 433/215 |
| 2012/0219924 A1* | 8/2012 | Walsh | .................... | A61C 1/088 433/29 |
| 2013/0034826 A1* | 2/2013 | Walsh | .................... | A61B 1/043 433/29 |
| 2015/0297089 A1* | 10/2015 | Deane | .................. | A61B 5/0088 433/27 |

FOREIGN PATENT DOCUMENTS

| | | |
|---|---|---|
| JP | 2004-521714 A | 7/2004 |
| JP | 2004-313783 A | 11/2004 |
| JP | 2010-152367 A | 7/2010 |
| JP | 2011-131057 A | 7/2011 |
| JP | 2013-034569 A | 2/2013 |
| JP | 2013-505084 A | 2/2013 |
| WO | 99/59462 A1 | 11/1999 |
| WO | 2011/035372 A1 | 3/2011 |
| WO | 2014/097135 A1 | 6/2014 |

OTHER PUBLICATIONS

Written Opinion of the International Searching Authority for PCT/JP2016/056112, dated May 24, 2016.
European Patent Office, extended European search report for European Patent Application No. 16758892.0, dated Oct. 10, 2018.

* cited by examiner

|     | I    | λ(nm) |
|-----|------|-------|
| t1  | 4533 | 405   |
| p1' | 2925 | 405   |
| t2  | 4289 | 465   |
| t2' | 1687 | 465   |

| t1/t2           | 1.055 |
|-----------------|-------|
| t2'×t1/t2       | 1779  |
| Δp (=p1'−t1')   | 1146  |

OPTICAL MEASURING DEVICE AND TOOTHBRUSH PROVIDED WITH SAME

TECHNICAL FIELD

The present invention relates to an optical measuring device that detects examined light generated from dental plaque adhering to a tooth.

BACKGROUND ART

When dental plaque adhering to teeth is left undisturbed, bacteria in the dental plaque grow, thereby causing tooth decay and periodontal diseases. Proper removal of dental plaque by daily toothbrushing is important for prevention of such tooth decay and periodontal diseases. For effective toothbrushing, manners of moving toothbrushes are devised, and electric toothbrushes are used; however, portions with much dental plaque and portions with little dental plaque are often brushed only for a certain time on an average. Brushing the portions with little dental plaque leads to negative effects of excessive brushing, while the portions with much dental plaque are insufficiently brushed.

Dental plaque can be effectively removed in a short time by concentratedly brushing a portion to which the dental plaque adheres while monitoring the adhering amount of the dental plaque. Therefore, several methods for optically detecting dental plaque have been conventionally proposed. Typical examples thereof include a method utilizing the fact that bacteria included in dental plaque or bacteria in dental caries produce protoporphyrin IX (hereinafter referred to as "PPIX"), which is a fluorescent substance, in the intraoral environment. A fluorescence measuring method has been known in which a tooth is irradiated with excitation light having a certain wavelength, and fluorescence emitted by a fluorescent substance is detected, thereby quantitating the amount of dental plaque or the degree of dental caries.

For example, fluorescence spectra from enamel obtained by irradiating the enamel of a healthy tooth and the enamel of a carious tooth only with excitation light having a wavelength of 406 nm are illustrated in Patent Literature 1. Peaks at wavelengths of 636 nm and 673 nm indicate fluorescent emissions peculiar to carious enamel. Measurement of such fluorescence enables discrimination between the enamel of a healthy tooth and the enamel of a carious tooth. It is found that examination of a fluorescence spectrum is effective for diagnosing dental caries, because the shape of the fluorescence spectrum is obviously changed due to a worsening of dental caries. In addition, Patent Literature 1 describes a method in which the amount S1 of fluorescence having a wavelength band of 636 nm or 673 nm and the amount S2 of fluorescence having a band of 550 nm are measured using a filter, and the ratio S1/S2 thereof is used for quantitative evaluation of dental caries.

The autofluorescence spectrum of a tooth from a tooth surface from which a biological deposit has been removed, and a fluorescence spectrum from a tooth surface covered with a new dental plaque layer are illustrated in Patent Literature 2. The spectra are measured using an excitation light sources at a wavelength of 420 nm or less. In addition, Patent Literature 2 illustrates a magnified view of a region indicating the intensity of autofluorescence at a wavelength longer than 530 nm, and represents that the autofluorescence intensity is decreased with gradually increasing a biological deposition layer. This can be understood to be because excitation light is absorbed or scattered by the dental plaque layer, whereby the intensity of excitation light arriving at the tooth surface is decreased, and thus the autofluorescence from the tooth is reduced.

Patent Literature 2 also describes that the maximum values of strongly emitted light are observed at 530 nm and 630 nm in a fluorescence spectrum obtained from a test tooth surface with a thick layer of a biological deposit considered to be new dental plaque. In the optical system of Patent Literature 2, fluorescence from dental plaque is not directly detected, but a tooth is irradiated with blue light at 480 nm, and the autofluorescence components of the tooth in reflected light are measured using a dichroic mirror. Then, a change in the intensity of autofluorescence from the tooth in movement of a toothbrush along the tooth in toothbrushing is observed to determine whether there is a biological deposition layer or not.

Patent Literature 3 describes a method for preventing the amount of plaque detected by a toothbrush-type plaque detection device from changing even when a distance between a tooth and a toothbrush is changed. Patent Literature 3 primarily describes a method for quantifying secondary fluorescence from a fluorescent agent bound to plaque. This method compensates for an apparent variation in the amount of plaque due to the distance by using a signal from an amplifier, i.e., the total amount of the fluorescence components and reflection components of excitation light. A compensated plaque value is determined using a compensation equation in which a coefficient has been determined by measurement performed in advance.

CITATION LIST

Patent Literature

Patent Literature 1: Japanese Examined Patent Publication (Kokoku) No. 6-73531 (page 1, FIG. 4)

Patent Literature 2: Published Japanese Translation of International Publication for Patent Application (Kohyo) No. 2002-515276 (page 1, FIG. 1)

Patent Literature 3: Japanese Unexamined Patent Publication (Kokai) No. 2011-131057 (page 1, FIG. 1)

SUMMARY

When the amount of dental plaque adhering to a tooth is small, the intensity of intrinsic fluorescence from the tooth is high, and fluorescence originating from the dental plaque is very weak in fluorescence obtained by irradiating, with excitation light, a portion to which the dental plaque adheres. The weak fluorescence originating from the dental plaque is superimposed on the strong intrinsic fluorescence from the tooth, in view of the wavelength band (630 to 680 nm) of the fluorescence from the dental plaque. A technique that can effectively separate and detect the weak fluorescence and the strong intrinsic fluorescence is demanded. In addition, a simple configuration in which such a mechanism is easily incorporated into a toothbrush is demanded.

The conventional technologies are considered from the above viewpoint as follows: in the configuration of Patent Literature 1, when the amount of dental plaque adhering to a surface of a tooth is small, the amount of detected fluorescence is changed by the influence of environmental light and a distance between the tooth and a detector due to little fluorescence from the dental plaque, and it is therefore difficult to detect a slight amount of dental plaque adhering to a surface of a healthy tooth. The configuration of Patent Literature 1 has the effect of compensating for a fluctuation due to a distance between a tooth and the detector by determining the ratio S1/S2 between the fluorescence intensities in the two wavelength regions selected by the optical filter among fluorescence intensities obtained by irradiating the tooth with light at a certain wavelength. However, in order that the fluorescence components may be selected as components in the two wavelength regions, the configuration of the optical filter is complicated, which may become an impediment to incorporation of the optical filter into a toothbrush.

In the configuration of Patent Literature 2, when the amount of dental plaque is small, the amount of change in the attenuation of intrinsic fluorescence is also small, and a measurement error may therefore be increased due to the influence of a distance between a detection unit and a tooth, generated by movement of a brush in toothbrushing. Primarily, there is concern about no detection of fluorescence proportional to the amount of bacteria causing tooth decay and periodontal diseases.

In the configuration of Patent Literature 3, it may be difficult to detect a small amount of dental plaque, because the amount of fluorescence including intrinsic fluorescence from a tooth is primarily measured as the amount of the plaque. The compensation for the amount of the plaque due to the distance is effective; but there remains a possibility that an error is caused due to an individual difference in the case of incorporation into the toothbrush, a positional relationship between the toothbrush and the tooth, and the like because the coefficient in the compensation equation is determined by the measurement performed in advance.

As described above, the conventional technologies do not provide a method that can properly detect a small amount of dental plaque. An object of the present invention is to provide an optical measuring device that can properly detect a small amount of dental plaque, can be easily incorporated into a toothbrush, and has a simple configuration.

Provided is a fluorescence measuring device that irradiates a sample with light having wavelengths different from each other and measures intensities of fluorescence generated from the sample, the fluorescence measuring device including a first light source that emits light having a first wavelength, a second light source that emits light having a second wavelength longer than the wavelength of the light emitted by the first light source, a detection unit that detects intensities of fluorescence generated when the same sample is irradiated with the light having the first wavelength and the light having the second wavelength, and a control unit that calculates an amount of fluorescent substance to be measured, based on a first intensity of fluorescence detected by the detection unit when the sample is irradiated with the light having the first wavelength and a second intensity of fluorescence detected by the detection unit when the sample is irradiated with the light having the second wavelength.

Provided is an optical measuring device including a plurality of light sources that irradiate a sample with light having a plurality of wavelengths different from each other, respectively, a detection unit that detects intensities of examined light generated when the sample is irradiated with the light having the plurality of wavelengths, and a control unit that calculates an amount of fluorescent substance to be measured, based on the intensities of the examined light detected by the detection unit in response to the light having the plurality of wavelengths.

Preferably, in the above optical measuring device, the plurality of light sources include a first light source that emits light having a first wavelength, and a second light source that emits light having a second wavelength longer than the wavelength of the light emitted by the first light source, the detection unit detects a first intensity of fluorescence generated when the sample is irradiated with the light having the first wavelength, and a second intensity of fluorescence generated when the sample is irradiated with the light having the second wavelength, and the control unit calculates the amount of the fluorescent substance using a difference or ratio between the first intensity of the fluorescence and the second intensity of the fluorescence.

Preferably, in the above optical measuring device, the sample is irradiated alternately with the light having the first wavelength and the light having the second wavelength.

Preferably, in the above optical measuring device, the first wavelength is a wavelength in a range from 350 nm to 430 nm, and the second wavelength is a wavelength in a range from 435 nm to 500 nm.

Preferably, in the above optical measuring device, the first and second wavelengths are wavelengths in a range from 350 nm to 430 nm, and a difference between the first wavelength and the light of the second wavelength is 5 nm or more.

Preferably, the above optical measuring device further includes a color mixture unit that uniformalizes intensity distributions in a surface irradiated with the light emitted from the first light source and the second light source.

Preferably, in the above optical measuring device, the detection unit includes an optical filter for receiving light that cuts a wavelength region excluding a range of a wavelength of fluorescence emitted by a fluorescent substance to be measured, contained in the sample.

Preferably, the above optical measuring device further includes an optical filter for emitting light that cuts a wavelength region excluding the wavelengths of the light from the first light source and the second light source.

Preferably, in the above optical measuring device, the plurality of light sources include an optical waveguide for emitting light, through which the light having the first wavelength and the light having the second wavelength with which the sample is irradiated are guided, the detection unit includes an optical waveguide for receiving light, through which the detected examined light is guided, and the optical waveguide for emitting light and the optical waveguide for receiving light are formed by a same optical waveguide.

Preferably, in the above optical measuring device, the plurality of light sources include a first light source that emits light having a first wavelength, and a second light source that emits light having a second wavelength longer than the wavelength of the light emitted by the first light source, the detection unit detects a first intensity of light reflected when the sample is irradiated with the light having the first wavelength, and a second intensity of light reflected when the sample is irradiated with the light having the second wavelength, and the control unit calculates the amount of the fluorescent substance using a difference or ratio between the first intensity of the reflected light and the second intensity of the reflected light.

The above optical measuring device can also be included in a toothbrush.

DESCRIPTION OF EMBODIMENTS

Hereinafter, with reference to the drawings, optical measuring devices and optical measuring methods will be explained in detail. However, the technical scope of the present invention is not limited to embodiments thereof, and includes the invention described in the claims and equivalents thereof.

Principle

First, the principle of the optical measuring method will be described with reference to FIG. 1 and FIG. 2. This optical measuring method includes: alternately irradiating the same tooth with excitation light having two different wavelengths; detecting fluorescence generated on the tooth due to the excitation light having the respective wavelengths, in a fluorescence wavelength region originating from dental plaque; and separating and detecting fluorescence to be measured that is superimposed on intrinsic fluorescence from the tooth and originates from the dental plaque, by using a ratio or difference between the intensities of the fluorescence.

Figure 1:
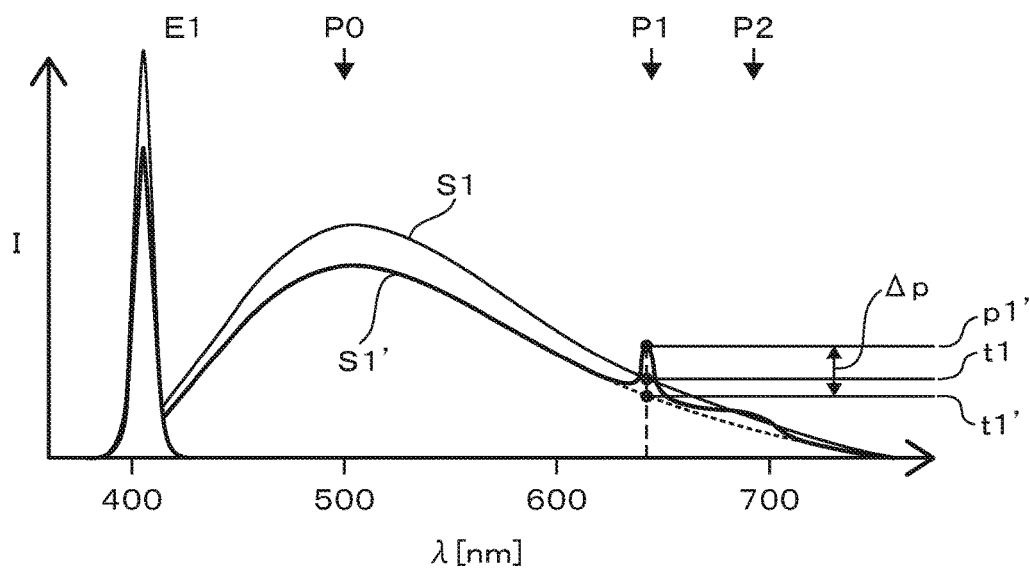
FIG. 1 is a graph illustrating the spectra of light obtained from a clean tooth and a tooth to which dental plaque adheres, respectively, when the teeth are irradiated with purple light.

FIG. 1 is a graph illustrating the spectra of light obtained from a clean tooth and a tooth to which dental plaque adheres, respectively, when the teeth are irradiated with purple light having a peak wavelength of 405 nm as a first wavelength. The horizontal axis of the graph indicates a wavelength $\lambda$ (nm), while the vertical axis of the graph indicates a fluorescence intensity I which is a first fluorescence intensity. A thin line represents a spectrum S1 obtained from the clean tooth, while a thick line represents a spectrum S1' obtained from the tooth to which the dental plaque adheres. A peak E1 at around 405 nm represents excitation light detected due to reflection or scattering of purple light of 405 nm, with which the irradiation has been performed, by a tooth surface. Broad fluorescence having a peak P0 at around 500 nm is intrinsic fluorescence from the teeth. Peaks P1 and P2 at around 635 nm and around 675 nm represent fluorescence spectra obtained from a fluorescent substance PPIX included in the dental plaque.

The peaks P1 and P2 originating from the dental plaque are not observed in the spectrum S1 obtained from the clean tooth, whereas the peaks P1 and P2 of fluorescence originating from the dental plaque are observed in the spectrum S1' obtained from the tooth to which the dental plaque adheres. The spectrum S1' undergoes a uniform attenuation in the entire wavelength region in comparison with the spectrum S1. This attenuation is an attenuation caused by absorption of excitation light by the adhering dental plaque, depends on the amount of the dental plaque, and represents an approximately uniform attenuation without depending on a wavelength.

In order to measure the peak P1 of the fluorescence originating from the dental plaque with higher precision, it is necessary to determine the amount Δp of fluorescent substance originating from the dental plaque, obtained by subtracting the component t1' of the intrinsic fluorescence from the teeth, from a spectrum intensity p1' at the wavelength of the peak P1, as represented in the following mathematical expression (1).

$$\Delta p1 = p1' - t1' \tag{1}$$

In other words, it is necessary to determine the component t1' of the intrinsic fluorescence from the teeth in a state in which the dental plaque adheres and without causing fluorescence originating from the dental plaque. As a result of intensive examination of such conditions, it was found that it is preferable to acquire a spectrum obtained by using a light source having a second wavelength which is a longer wavelength than the first wavelength, which is 405 nm in this case.

Figure 2:
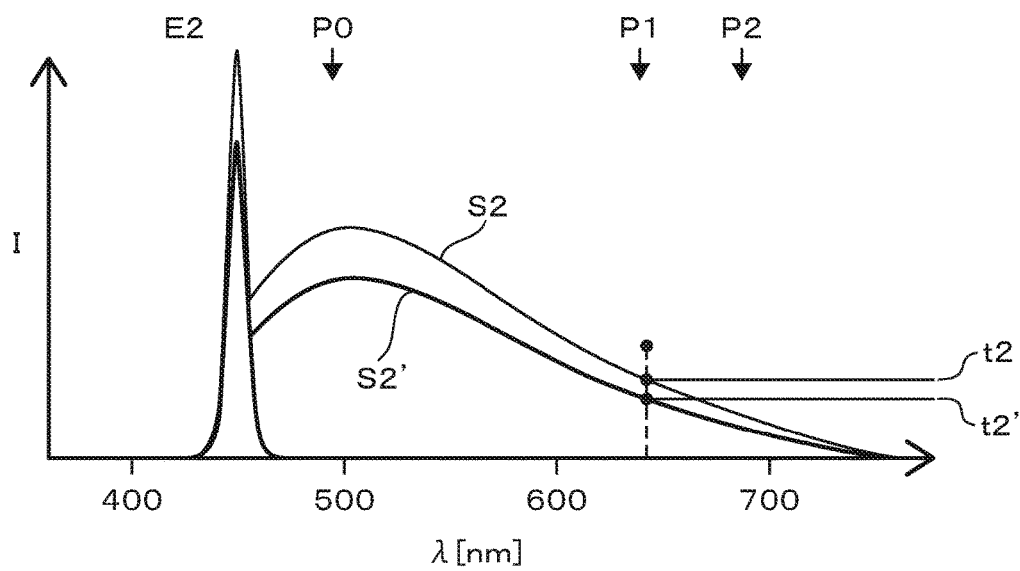
FIG. 2 is a graph illustrating the spectra of light obtained from a clean tooth and a tooth to which dental plaque adheres, respectively, when the teeth are irradiated with blue light.

FIG. 2 is a graph illustrating the spectra of light obtained from a clean tooth and a tooth to which dental plaque adheres, respectively, when the teeth are irradiated with blue light having a peak wavelength of 465 nm as a second wavelength. Like FIG. 1, the horizontal axis of the graph indicates a wavelength λ (nm), while the vertical axis of the graph indicates a fluorescence intensity I which is a second fluorescence intensity. A thin line represents a spectrum S2 obtained from the clean tooth, while a thick line represents a spectrum S2' obtained from the tooth to which the dental plaque adheres.

When the clean tooth and the tooth to which the dental plaque adheres are irradiated with blue light having a wavelength of 465 nm, the broad peak P0 of intrinsic fluorescence from the teeth is observed similarly in the case of the irradiation with purple light having a wavelength of 405 nm; however, since PPIX is weakly excited, peaks P1 and P2 originating from the dental plaque are not observed. Accordingly, the component t2' of the intrinsic fluorescence from the teeth excited at the second wavelength can be substituted for the component t1' of the intrinsic fluorescence excited at the first wavelength, and the amount Δp of fluorescent substance originating from the dental plaque can be determined on an approximate basis by the following mathematical expression (2).

$$\Delta p \approx p1' - t2' \qquad (2)$$

In order to achieve such an approximation, it is necessary to uniformalize the components t1' and t2' of the intrinsic fluorescence by adjusting in advance the intensities of excitation light at the first wavelength and the second wavelength. The intensities of excitation light may be adjusted, using the proportional relation of the attenuation of intrinsic fluorescence with respect to the amount of dental plaque, so that the components t1 and t2 of the intrinsic fluorescence, measured on the clean teeth, are equal to each other. Alternatively, such a correction as described in the following mathematical expression (3) can be made by measuring the ratio t1/t2 between the components t1 and t2 of the intrinsic fluorescence from the clean teeth in advance.

$$\Delta p \approx p1' - t2' \times (t1/t2) \qquad (3)$$

On the basis of the principle described above, the fluorescence that is superimposed on the intrinsic fluorescence from the teeth and originates from the dental plaque can be separated and detected by alternately irradiating the teeth with the excitation light having the two different wavelengths, detecting, in the fluorescence wavelength region originating from the dental plaque, fluorescence generated on the teeth by the excitation light having the respective wavelengths, and using a ratio or difference between the first fluorescence intensity and the second fluorescence intensity which are the intensities of the fluorescence.

First Embodiment

Figure 3:
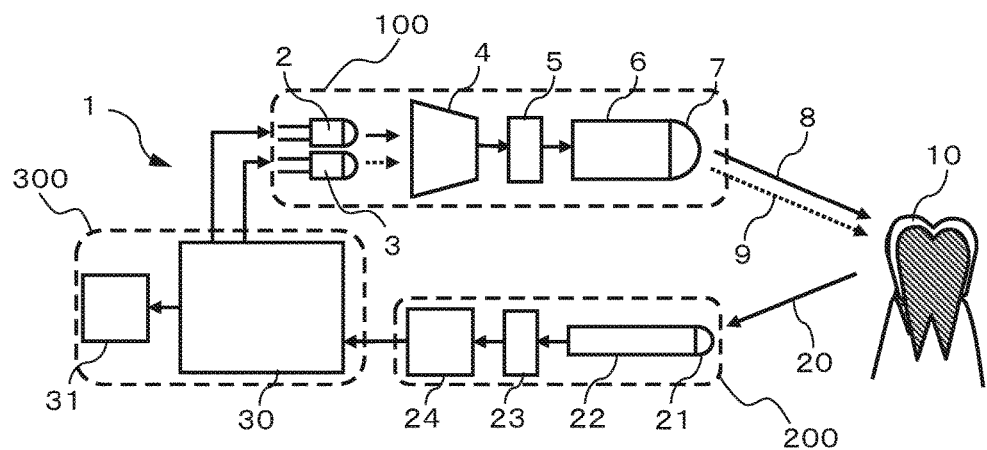
FIG. 3 is a configuration view of a fluorescence measuring device 1.

A fluorescence measuring device for actualizing the principle of the optical measuring method described above will now be described with reference to the drawings. FIG. 3 is a configuration view of a fluorescence measuring device 1. The fluorescence measuring device 1 is an example of optical measuring devices using fluorescence as examined light. The fluorescence measuring device 1 includes three blocks of a light source unit 100 for exciting a fluorescent substance included in dental plaque, a detection unit 200 for detecting the intensities of fluorescence generated on a tooth surface, and a control unit 300 for determining the adhering amount of the dental plaque from the measured fluorescence intensities and notifying a user of the amount.

The light source unit 100 includes a first light source 2 that emits light at a first wavelength, a second light source 3 that emits light at a second wavelength, a color mixture unit 4, an optical filter 5 for emitting light, an optical waveguide 6 for emitting light, and a light condensation unit 7 for emitting light. The color mixture unit 4, the optical filter 5 for emitting light, the optical waveguide 6 for emitting light, and the light condensation unit 7 for emitting light are included in a light path portion for irradiating a tooth to be measured with light from the first light source 2 and the second light source 3.

Light-emitting diodes and semiconductor lasers which are small-sized and inexpensive can be used as the first light source 2 and the second light source 3. The wavelengths of light generated by the first light source 2 or the second light source 3 are selected as follows. The first wavelength is included in wavelengths with high excitation efficiency for a fluorescent substance included in dental plaque, and the second wavelength is set at a wavelength which is longer than the first wavelength and of which the excitation efficiency is lower than that of the first wavelength or is approximately zero. The first wavelength is preferably in a range from 350 nm to 430 nm, and the second wavelength is preferably in a range from 435 nm to 500 nm. As a specific example, the first light source 2 may be a purple LED having a peak wavelength of 405 nm, and the second light source 3 may be a blue LED having a peak wavelength of 465 nm.

The color mixture unit 4 has the function of uniformalizing light intensity distributions in a surface irradiated with light between light having the first wavelength and light having the second wavelength, in order to prevent color unevenness from occurring when the tooth to be measured is irradiated with light generated by the first light source 2 and the second light source 3. It is important to allow the light intensity distributions between light having the first wavelength and light having the second wavelength to be coincident with each other, and it is allowable that the light intensity distributions are present. Therefore, the freedom of design of the color mixture unit 4 becomes relatively higher.

The optical filter 5 for emitting light is a filter through which light from the first light source 2 and the second light source 3 passes, and which cuts fluorescence in a wavelength region originating from dental plaque. When a short-pass filter is used as the optical filter 5 for emitting light, it is preferable to select a cutoff wavelength that is sufficiently longer than the second wavelength and is sufficiently shorter than the fluorescence wavelength of a fluorescent substance included in dental plaque. In the present embodiment, the setting of cutting wavelengths of 500 nm or more is performed.

The optical waveguide 6 for emitting light is used for guiding light from the first light source 2 or the second light source 3 to the vicinity of the tooth to be measured without attenuating the light. Plastic or glass can be used as the material of the optical waveguide 6 for emitting light. It is more preferable to form a mirror coating on the outer periphery of the optical waveguide 6 for emitting light, thereby preventing light from leaking. A hollow optical waveguide surrounded by a mirror, such as a light pipe, can also be used as the optical waveguide 6 for emitting light.

The light condensation unit 7 for emitting light includes a lens for condensing, into about the size of a tooth, light which propagates into the optical waveguide 6 for emitting light, and for performing irradiation with the light.

The detection unit 200 includes a light condensation unit 21 for receiving light, an optical waveguide 22 for receiving light, an optical filter 23 for receiving light, and a light detector 24.

The light condensation unit 21 for receiving light condenses examined light 20 including fluorescence generated on the tooth. The optical waveguide 22 for receiving light is, together with the light condensation unit 21 for receiving light, included in a light path portion for allowing condensed light to propagate to the light detector 24. When the fluorescence measuring device 1 is incorporated into a toothbrush, the brush portion of the toothbrush may be used as the optical waveguide 22 for receiving light, and the leading end of the toothbrush may be used as the light condensation unit 21 for receiving light.

The optical filter 23 for receiving light is a filter for cutting wavelength components except fluorescence of interest. It is preferable to set the optical filter 23 for receiving light to cut a wavelength region excluding a range of 620 nm to 690 nm which is the wavelength region of fluorescence emitted by a fluorescent substance included in dental plaque. Since the reflected light of light from the light sources, directly reflected by the tooth, strongly appears particularly in a short-wavelength side, it is preferable to allow the optical filter 23 for receiving light to have sharp attenuation properties to cut the reflected light. Fluorescence spectra from dental plaque have two strong peaks at around 630 to 640 nm and around 670 to 680 nm, and an S/N ratio can be therefore improved by using, as the optical filter 23 for receiving light, a band-pass filter having transmittance properties similar to the shapes of the fluorescence spectra.

The control unit 300 includes a control circuit 30 and a notification unit 31.

The control circuit 30 controls the brightnesses and turning-on times of the first light source 2 and the second light source 3 to allow the tooth to be alternately irradiated with light having two wavelengths. Such differentiation between the turning-on time of the first light source 2 and the turning-on time of the second light source 3 enables fluorescence from a fluorescent substance, obtained by irradiating the tooth with the light from the respective light sources, to be received in distinction from each other. Assuming that the intensity of the fluorescence obtained by turning on the first light source 2 is P1 and the intensity of the fluorescence obtained by turning on the second light source 3 is P2, the control circuit 30 determines a ratio P1/P2 or difference (P1-P2) between the fluorescence intensities, thereby determining the amount of the fluorescent substance included in the dental plaque, as described in the section of the principle.

The notification unit 31 notifies a user of the toothbrush of the determined amount of the fluorescent substance. Buzzer sound, or electronic sound generated by using a piezoelectric element may be used in such notification. In the case of the electronic sound, feedback can be given to the user by changing the pitch or loudness of the sound, or the pitch of the intermittent sound according to the amount of the fluorescent substance. A voice messages generated by voice synthesis, music, or the like may also be used.

The control unit 300 may record the fluorescence intensities detected according to the light having the two wavelengths, respectively, and may perform averaging processing of the fluorescence intensities arbitrary times, whereby noise can be reduced. The control unit 300 may set the turning-on times of the first light source 2 and the second light source 3 at times different from the cycle of a commercial power supply, in order to avoid the influence of indoor light from a fluorescent lamp or the like, whereby the influence of illumination light can be reduced.

The control unit 300 may alternately perform irradiation with light emitted from the first light source 2 or the second light source 3 so that the light sources are turned off between the emissions of the light from the light sources, as needed. The influence of environmental light can be reduced by subtracting the amount of fluorescent substance, acquired by turning off the light sources, from the amount of fluorescent substance, acquired by turning on the first light source 2 or the second light source 3.

Second Embodiment

Figure 4A:
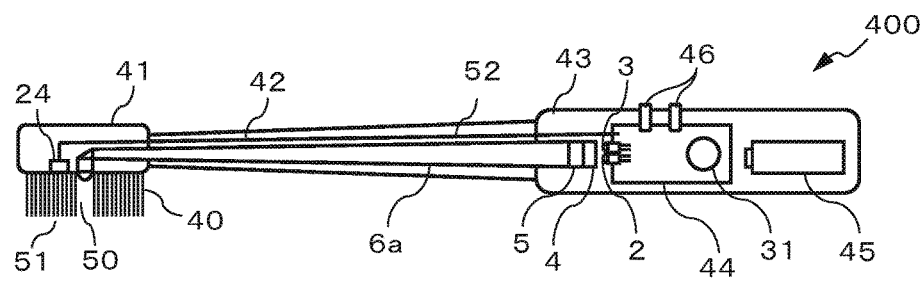
FIG. 4A is a configuration view of a toothbrush-type fluorescence measuring device 400.

A second embodiment in which a fluorescence measuring device is incorporated into a toothbrush will now be described with reference to the drawings. FIG. 4A is a configuration view of a toothbrush-type fluorescence measuring device 400, and FIG. 4B is a configuration view of the toothbrush head of the fluorescence measuring device 400.

The toothbrush-type fluorescence measuring device 400 is an example of optical measuring devices using fluorescence as examined light, and includes a toothbrush head 41, a stem unit 42, and a grip unit 43. A first light source 2 and a second light source 3, together with a control circuit 30 (see FIG. 3) and a notification unit 31, are placed on a circuit board 44 disposed in the grip unit 43. Light from the first light source 2 and the second light source 3 is guided to the toothbrush head 41 through a color mixture unit 4 and an optical filter 5 for emitting light, disposed in the grip unit 43, as well as an optical waveguide 6a for emitting light with a long tapered shape, disposed in the stem unit 42. The direction of the guided light is changed using means such as a mirror or the like in the toothbrush head 41, and a tooth surface is irradiated with the light as excitation light from a light irradiation unit 50 on the toothbrush head 41. Fluorescence generated on a tooth is guided to a light detector 24 through brushes 40 that are arranged in a light detection unit 51 of the toothbrush head 41 and are made of a material that transmits fluorescence.

Figure 4B:
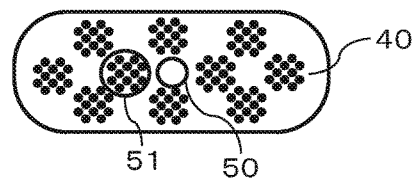
FIG. 4B is a configuration view of the toothbrush head of the fluorescence measuring device 400.

In the present embodiment, the light irradiation unit 50 is arranged in the center of the toothbrush head, and the light detection unit 51 is disposed adjacently to the light irradiation unit 50, as illustrated in FIG. 4B. However, the arrangement is not limited to such an example but encompasses various possible variations. For example, multiple light irradiation units 50 and light detection units 51 may be disposed in the toothbrush head, and the light irradiation units 50 and the light detection units 51 may be linearly alternately arranged.

Fluorescence detected by the light detector 24 is converted into photocurrent, which is passed to the circuit board 44 through a wiring 52. The amount of fluorescent substance is determined by the control circuit 30 disposed in the circuit board 44, and a user is notified of the amount of the fluorescent substance with buzzer, electronic sound, or the like by the notification unit 31.

In the grip unit 43, a battery 45 is placed as a power supply for driving the fluorescence measuring device 400. Further, two switches 46 are disposed in the grip unit 43. For example, a fluorescence measuring function can be switched on/off using one of the switches 46, and notification sound can be switched and fluorescence detection sensitivity can be adjusted using the other switch 46.

The detailed configuration of the color mixture unit 4 will be described with reference to FIG. 5A to FIG. 5C. It is important that the in-plane intensity distribution of light with which a tooth is irradiated from the first light source 2 or the second light source 3 is not changed in the fluorescence measuring device 400. Such unchangingness of the in-plane intensity distribution is an important factor for determining a detection limit. Therefore, it is necessary that the in-plane intensity distribution of irradiation light has no wavelength dependence in a stage in which light arrives at a light condensation unit 7 for emitting light disposed in the toothbrush head 41. The color mixture unit 4 performs the action of eliminating the wavelength dependence of the in-plane intensity distribution of irradiation light.

Figure 5A:
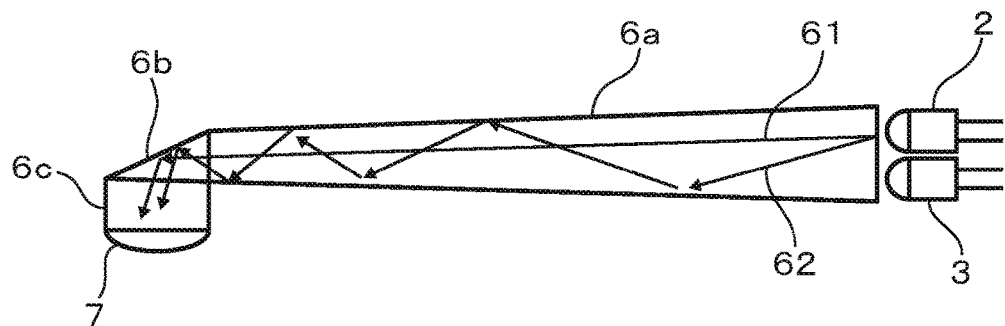
FIG. 5A is a view illustrating a configuration example of a color mixture unit using a light pipe with a tapered shape.

FIG. 5A is a view illustrating a configuration example of a color mixture unit using a light pipe with a tapered shape. A long optical path can be obtained by arranging a light pipe as the optical waveguide 6a for emitting light from the stem unit 42 to the toothbrush head 41 in the toothbrush-type fluorescence measuring device 400. Plurally repeated reflection of light from the first light source 2 or the second light source 3 in the light pipe results in uniformalization of the in-plane distribution of the light, and therefore enables the effect of color mixture to be easily enhanced. In other words, the optical waveguide 6a for emitting light itself functions as a color mixture unit. Light 62 obliquely emitted from the first light source 2 or the second light source 3 is repeatedly reflected plural times, while light 61 emitted approximately perpendicularly to an end face of the optical waveguide 6a for emitting light is reflected less times; however, the long optical path can result in effective color mixture.

The use of the light pipe with the tapered shape illustrated in FIG. 5A as the optical waveguide 6a for emitting light enables the optical waveguide 6a for emitting light to have the function of a color mixture unit even when the color mixture unit 4 is not separately disposed, and enables the in-plane intensity distribution of irradiation light to approximate uniformity in a simple configuration. Extremely obliquely emitted light is reflected many times in the light pipe, and the reflection loss of the light is therefore unignorable; however, use of shell-shaped LEDs with a low emission angle as the first light source 2 and the second light source 3 enables such a reflection loss to be reduced and optical coupling efficiency to be simultaneously increased.

The light pipe may be a hollow-type light pipe using a mirror or may be a plastic light pipe. When the light pipe is a plastic light pipe, leaking light can be reduced by coating the outer periphery of the light pipe with a metal mirror. The shape of the light pipe may be a simple linear shape or a tapered shape. The effect of the color mixture can be easily enhanced by disposing a regular or irregular reflection surface in the pipe. A cross-sectional shape of the light pipe may be a round shape, an elliptical shape, a rectangular shape, a polygonal shape, or the like, and it is also easy to properly use a structure suitable for the shape and design of a toothbrush from such various shapes.

Figure 5B:
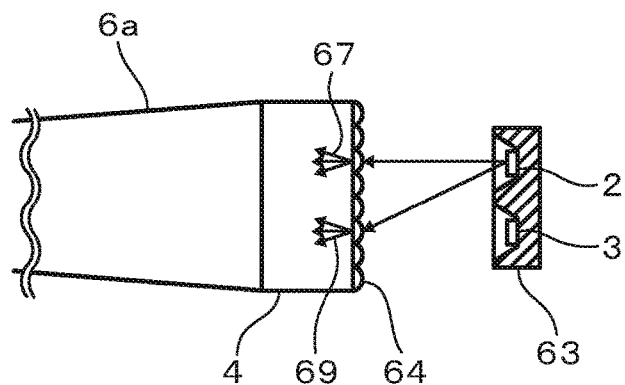
FIG. 5B is an explanatory diagram of a form in which the color mixture unit 4 is added to the optical waveguide 6a for emitting light illustrated in FIG. 5A.

FIG. 5B is an explanatory diagram of a form in which the color mixture unit 4 is added to the optical waveguide 6a for emitting light illustrated in FIG. 5A. In the example illustrated in FIG. 5B, a color mixture unit in which a microlens array 64 is arranged on an incidence end face is used as the color mixture unit 4. The effect of the color mixture is further enhanced by converting light from the first light source 2 or the second light source 3 into light 67 and 69 from multiple point light sources in such a manner.

In the example illustrated in FIG. 5B, LED chips as the first light source 2 and the second light source 3 are mounted on a substrate 63 with a mirror which is a 45-degree reflection mirror. Such a structure allows light emitted from the first light source 2 and the second light source 3 to be guided forward, and therefore results in a reduced emission angle. In addition, the use of the LED chips enables the spacing between the light sources to be decreased, and therefore enables the in-plane intensity distribution of irradiation light to further approximate uniformity.

Figure 5C:
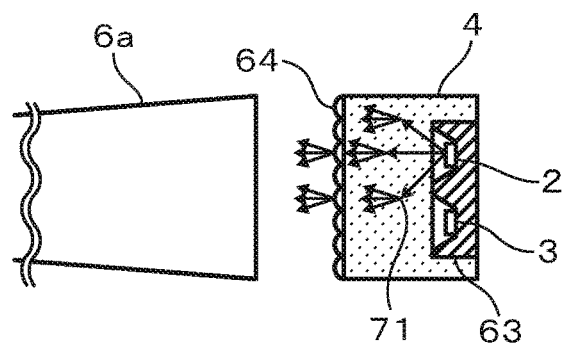
FIG. 5C is an explanatory diagram of a form in which a color mixture unit 4 having another configuration is added to the optical waveguide 6a for emitting light illustrating in FIG. 5A.

FIG. 5C is an explanatory diagram of a form in which a color mixture unit 4 having another configuration is added to the optical waveguide 6a for emitting light illustrating in FIG. 5A. In the example illustrated in FIG. 5C, a color mixture unit including a scatterer that scatters light emitted from the first light source 2 and the second light source 3 is used as the color mixture unit 4. This color mixture unit 4 is formed by sealing the first light source 2 and the second light source 3 placed in the substrate 63 with a mirror, with a transparent resin including light-scattering particles 71. The in-plane intensity distribution of irradiation light is enabled to approximate uniformity by allowing the many light-scattering particles 71 to multiply scatter light from each light source. Further, the microlens array 64 may be added to an emission end face of the color mixture unit 4, whereby the effect of the color mixture can be further enhanced.

Figure 6:
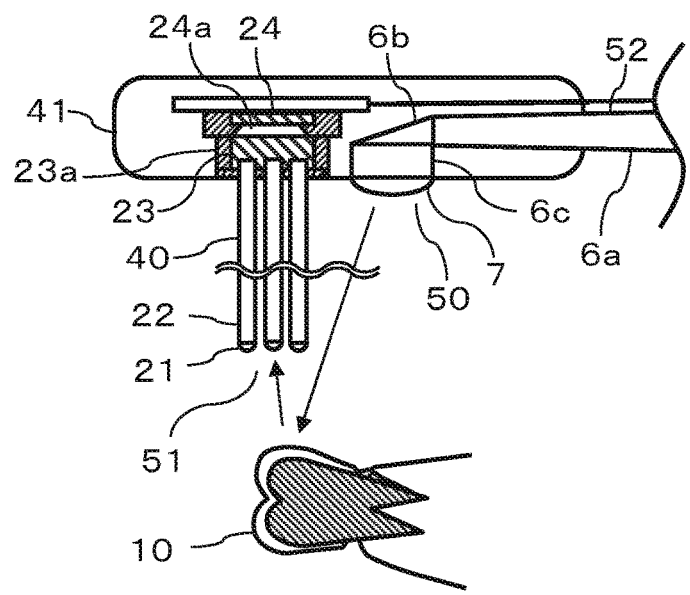
FIG. 6 is a configuration view illustrating the interior of the toothbrush head 41.

FIG. 6 is a configuration view illustrating the interior of the toothbrush head 41. The light passed through the optical waveguide 6a for emitting light changes its direction at a mirror 6b in the toothbrush head 41 and passes through an optical waveguide 6c for emitting light, and then a tooth 10 is irradiated with the light as excitation light from the light condensation unit 7 for emitting light. Fluorescence generated from dental plaque adhering to a surface of the tooth and the tooth in the vicinity of the dental plaque is detected by the light detector 24 through the brushes 40 and an optical filter 23 for receiving light. The leading ends of the brushes 40 are allowed to have a curvature, thereby functioning as light condensation units 21 for receiving light. The brushes 40 except the leading ends function as optical waveguides 22 for receiving light. A light-shielding body 23a is arranged to surround the optical filter 23 for receiving light. The light-shielding body 23a prevents environmental light and excitation light from being directly incident on the optical filter 23 for receiving light without through the brushes 40.

A scattering loss can be prevented by allowing the optical filter 23 for receiving light and end faces of the brushes 40 to adhere to each other with an optical adhesive having a refractive index close to the refractive indices of the brushes 40 and the optical filter 23 for receiving light. Alternatively, the end faces of the brushes 40 and an opening 24a of the light detector 24 can be allowed to adhere to each other with an optical adhesive having the function of the optical filter 23 for receiving light. A material functioning as an optical filter can also be used as the material of the brushes 40. In such a case, the end faces of the brushes 40 are arranged on the opening 24a of the light detector 24, and are allowed to adhere to the opening 24a with an optical adhesive.

Figure 7:
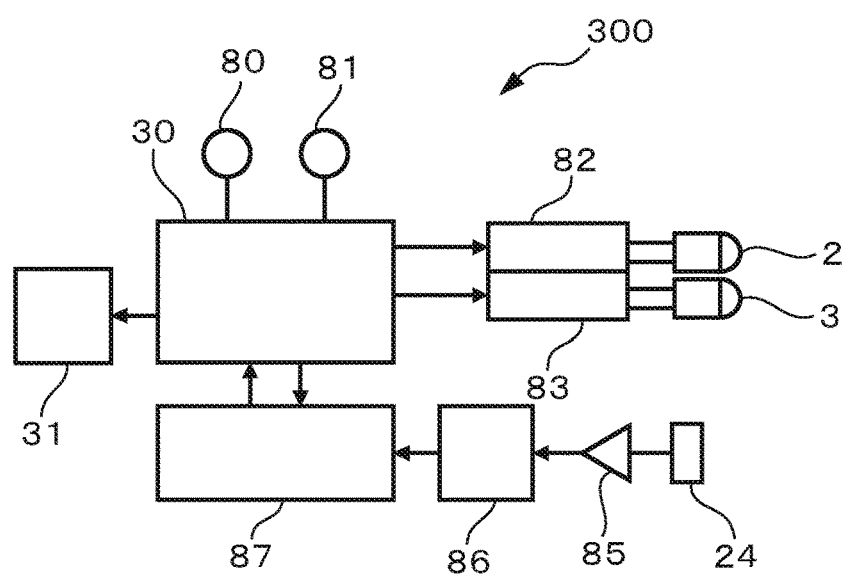
FIG. 7 is a block diagram illustrating an example of the circuit configuration of a control unit 300.

FIG. 7 is a block diagram illustrating an example of the circuit configuration of a control unit 300. The control unit 300 includes switches 80 and 81, light source drive circuits 82 and 83, an amplifier 85, an A/D converter 86, and a data-processing circuit 87, which are disposed on the circuit board 44 (see FIG. 4) in the grip unit 43.

The control circuit 30 controls the light source drive circuits 82 and 83 on the basis of a signal that controls the timing of turning on the first light source 2 and the second light source 3 and lighting intensities thereof. Light incident on the light detector 24 is converted into an electric signal by the amplifier 85, and the electric signal is converted into a digital signal by the A/D converter 86. The data-processing circuit 87 performs calculation for determining the amount of fluorescent substance on the basis of the digital signal. Specifically, the data-processing circuit 87 calculates the amount Δp of fluorescent substance originating from the dental plaque using the mathematical expression (3) described above. In addition, the data-processing circuit 87 stores a ratio t1/t2 between the components t1 and t2 of intrinsic fluorescence, measured in advance for a clean tooth.

The A/D converter 86 can be operated in synchronization with the timing of turning on the first light source 2 and the second light source 3, thereby digitally performing signal processing of the amount of fluorescent substance in light having a first wavelength and the amount of fluorescent substance in light having a second wavelength. Although the digital signal processing is adopted in the example illustrated in FIG. 7, equivalent processing may be performed as analog signal processing.

The switch 80 functions as an electric power switch. The switch 81 is used for the switching of notification sound, the setting of sensitivity, and the like.

The notification unit 31 may provide not only notification with the already described buzzer and electronic sound but also vibration notification using an eccentric motor, notification with LED flashing and light with a changed color tone, and notification with a language, graphics and a graph on a liquid crystal display. It is also acceptable to adopt a method in which wireless communication is used together in the notification unit 31, and notification information or information about the measurement is sent to an external instrument such as a mobile phone or a personal computer, thereby notifying a user with the external instrument.

Figure 8:
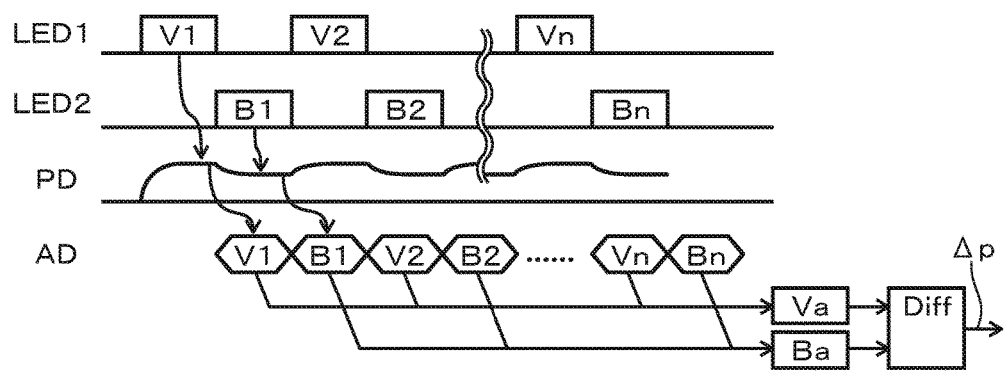
FIG. 8 is a timing chart representing the operation timing of the electronic circuits of the control unit 300.

FIG. 8 is a timing chart representing the operation timing of the electronic circuits of the control unit 300. In FIG. 8, the timing of turning on the first light source 2 is represented by LED1, and the timing of turning on the second light source 3 is represented by LED2. In the example represented in FIG. 8, LED1 and LED2 are alternately turned on n times, periods in which LED1 is turned on are denoted by V1 to Vn, and periods in which LED2 is turned on are denoted by B1 to Bn.

Fluorescence is generated from the tooth simultaneously with the tuning on of the first light source 2 or the second light source 3, detected by the light detector 24, and converted into an electric signal by the amplifier 85. In FIG. 8, the detected light signal is represented by PD. As such light signals PD, a high signal is output when LED1 is turned on, and a lower signal than the signal output when LED1 is turned on is output when LED2 is turned on. These signals are alternately output.

The analog light signals PD are converted into digital signals AD by the A/D converter 86 simultaneously with the ends of tuning-on cycles. Then, a digital average circuit Va averages the n items of data of V1 to Vn acquired when LED1 is turned on, thereby removing noise included in the signals. Similarly, a digital average circuit Ba averages the n items of data of B1 to Bn acquired when LED2 is turned on, thereby removing noise included in the signals.

Then, a subtraction processing circuit Diff determines a difference signal of the signals from which the noise has been removed. As a result, the amount Δp of fluorescent substance originating from dental plaque, obtained by subtracting, from measured fluorescence, intrinsic fluorescence from the tooth, can be determined.

The effect of removing the influence of environmental light can also be obtained by the subtraction processing, when an environmental light component added in the period in which LED1 is turned on and an environmental light component added in the period in which LED2 is turned on are almost the same.

A component that changes with moving a toothbrush and a component that relates to the frequency of a commercial power supply due to a fluorescent lamp or the like can be considered as the influence due to environmental light. In order to remove the influence of the latter component, the LEDs may be turned on at a sufficiently higher frequency than the frequency of the commercial power supply. Alternatively, fluctuations may be averaged by turning on the LEDs for time over multiple cycles, with the utilization of regular fluctuations. In order to remove the influence of the former component, it is preferable to reduce the turning-on period so that the LEDs are turned on at a sufficiently higher speed than the speed of the movement of the toothbrush, because the former component irregularly fluctuates.

When it is necessary to make a correction for the emission intensities of LED1 and LED2, the correction may be made by multiplying such an emission intensity by a certain coefficient in the digital average circuit Va or Ba. In accordance with the mathematical expression (3), such an emission intensity may be multiplied by a ratio t1/t2 between the components t1 and t2 of intrinsic fluorescence in the digital average circuit Ba. Alternatively, such an emission intensity may be multiplied by the coefficient t2 in the digital average circuit Va, and may be multiplied by the coefficient t1 in the digital average circuit Ba.

However, since it is impossible to obtain the effect of eliminating the influence of environmental light when the above-described correction is made, it is preferable to make such a correction by adjusting the intensities of the LED light sources. Alternatively, although not illustrated, the influence of environmental light may be eliminated by inserting turning-off periods between the periods in which the LEDs are turned on, and subtracting digital signals AD in the most recent turning-off periods from the digital signals AD in the turning-on periods. Such elimination enables a correction in a digital average circuit.

The amount Δp of the fluorescent substance originating from the dental plaque, obtained by the method described above, is sent to the control circuit 30. Processing and storage of the data are carried out in the control circuit 30, and a user is notified of the data by the notification unit 31.

In the above description, the processing is performed using the difference in order to obtain the amount Δp of the fluorescent substance originating from the dental plaque; however, when the adhering amount of the dental plaque is intended to be evaluated using the ratio between the amount of the fluorescent substance originating from the dental plaque and the amount of the fluorescent substance originating from the tooth, the control circuit may be changed to perform division processing instead of the subtraction processing Diff.

A fluorescence measuring device for confirming the principle of the optical measuring method described above was produced, and an experiment was carried out in which an actual tooth was irradiated with excitation light having the first wavelength and excitation light having the second wavelength, and fluorescence spectra from the tooth were measured.

Shell-shaped LEDs having a diameter of 3 mm were used as the light sources. In consideration of the availability of the LEDs, the wavelength of the first light source 2 was set at 405 nm (purple), and the wavelength of the second light source 3 was set at 465 nm (blue). In order to irradiate a tooth surface with excitation light with a mixed color, three purple LEDs and three blue LEDs were equally spaced in an alternating manner on six places on a circumference having a radius of 3 mm to make an LED ring, and a plastic plate with a scattering effect was further arranged as the color mixture unit 4 on the front faces of the LEDs. The optical filter 5 for emitting light was not used, because the full-widths at half maximum of the emission spectra of the LED light sources used in the experiment were as low as 30 nm or less. Such an optical system was arranged so that the tooth surface could be uniformly irradiated with light with a mixed color.

A plastic fiber having a core diameter of 1 mm was used as the optical waveguide 22 for receiving light, and arranged at the center of the LED ring. A scatter plate abutting on the front face of the fiber for receiving light was removed. An optical filter cutting wavelengths of 540 nm or less was used as the optical filter 23 for receiving light, and inserted into some midpoint of the optical fiber as the optical waveguide 22 for receiving light, thereby cutting the wavelength components of excitation light. A fiber light-receiving type spectroscope was used as the light detector 24, and an integral time was set at 50 mS.

A personal computer was used for measurement control and data processing. A stable light intensity was obtained by driving each LED with a constant current using a constant current source. A procedure was repeated five times by a computer program in which a current was passed to each LED in the order of turning on the purple LEDs, turning off all the LEDs, turning on the blue LEDs, and turning off all the LEDs. The turning-on time of each LED was set at 50 mS, and both of the LED currents passed to the purple LEDs and the blue LEDs were set at 10 mA. Spectra obtained by the spectroscope were captured into the computer through a USB interface, and data processing of the spectra was carried out.

A spectrum obtained by subtracting, from the spectrum captured when the purple LEDs were turned on, the spectrum captured when all the LEDs were subsequently turned off, thereby eliminating the influence of environmental light, was regarded as one fluorescence spectrum obtained when the purple LEDs were turned on. An average spectrum of such five fluorescence spectra was determined. Similar processing was carried out for the blue LEDs, thereby determining an average spectrum. The spectra determined in such a manner are illustrated in FIG. 9 and FIG. 10.

Figure 9:
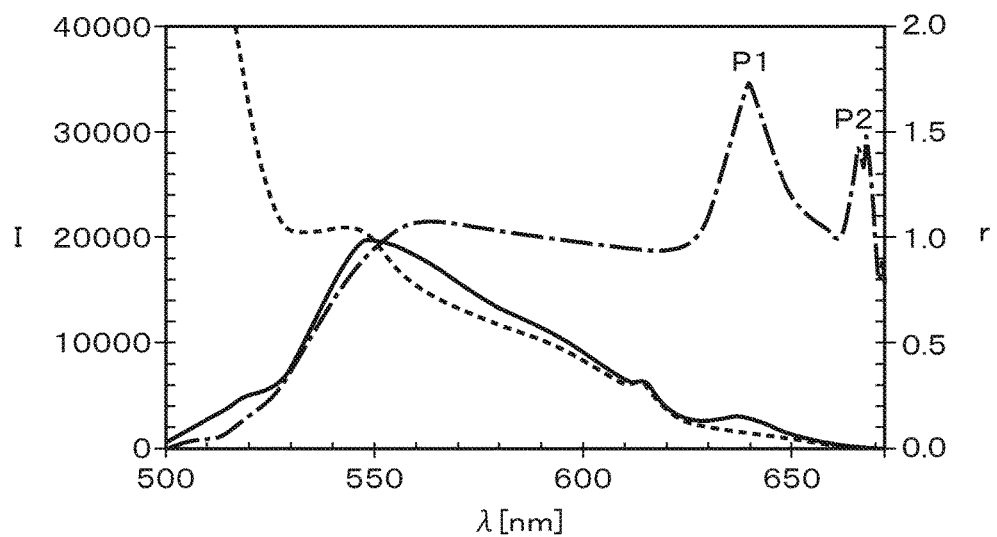
FIG. 9 is a graph illustrating examples of fluorescence spectra obtained by measuring a tooth to which dental plaque adhered.
Figures 10, 11:
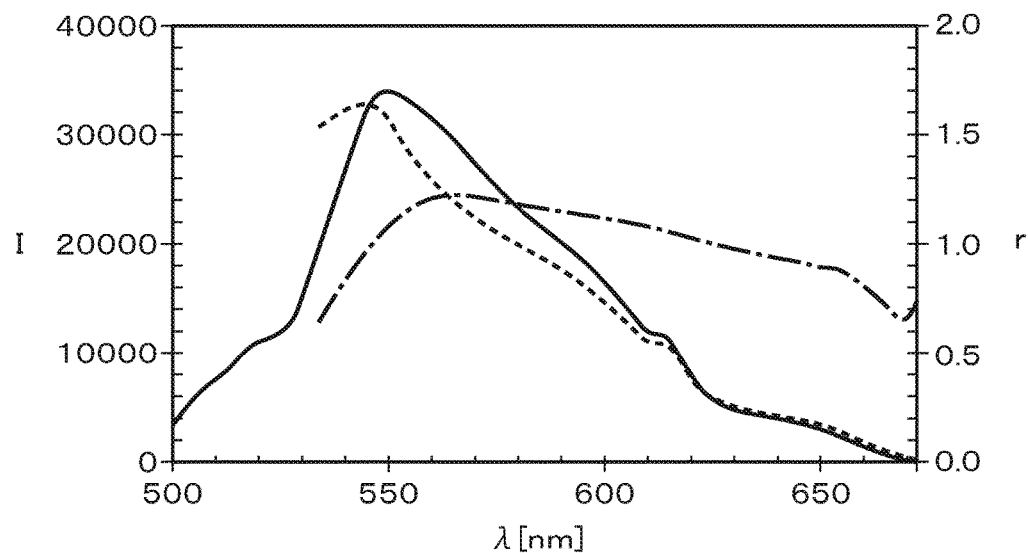
FIG. 10 is a graph illustrating examples of fluorescence spectra obtained by measuring a clean tooth.
FIG. 11 is a table representing the result of the quantified amount Δp of fluorescent substance originating from the dental plaque, based on the spectra of FIG. 9 and FIG. 10.

FIG. 9 is a graph illustrating examples of fluorescence spectra obtained by measuring a tooth to which dental plaque adhered, and FIG. 10 is a graph illustrating examples of fluorescence spectra obtained by measuring a clean tooth. The horizontal axis of each graph indicates a wavelengths λ (nm), and the vertical axis of each graph indicate a fluorescence intensity I and a fluorescence intensity ratio r. The fluorescence intensity I is plotted with digital data (count value) from a 16-bit A/D converter incorporated into the spectroscope. In FIG. 9 and FIG. 10, the solid lines represent spectra obtained by irradiation with light having a wavelength of 405 nm, and the dotted lines represent spectra obtained by irradiation with light having a wavelength of 465 nm. Each alternate long and short dash line represents the ratio r of both the fluorescence intensities, i.e., a value obtained by dividing the fluorescence intensity I obtained by the irradiation with light having a wavelength of 405 nm by the fluorescence intensity I obtained by the irradiation with light having a wavelength of 465 nm.

The combination of data described in each graph for the spectra of FIG. 9 and FIG. 10 and the combination of data described in each graph for the spectra of FIG. 1 and FIG. 2 used for describing the principle are different from each other. FIG. 9 corresponds to a plot of the spectrum S1' of FIG. 1 and the spectrum S2' of FIG. 2, and FIG. 10 corresponds to a plot of the spectrum S1 of FIG. 1 and the spectrum S2 of FIG. 2.

In the fluorescence intensity ratio r of the tooth to which the dental plaque adhered, represented in FIG. 9, the peaks P1 and P2 of the fluorescence originating from the dental plaque were clearly observed at around 639 nm and around 667 nm. In the fluorescence intensity ratio r of the clean tooth, represented in FIG. 10, the peaks P1 and P2 of the fluorescence originating from the dental plaque were not observed, although intrinsic fluorescence from the tooth was seen.

FIG. 11 is a table representing the result of the quantified amount Δp of fluorescent substance originating from the dental plaque, based on the spectra of FIG. 9 and FIG. 10. The intensity t1 of fluorescence from the clean tooth irradiated with light having the first wavelength, the intensity p1' of fluorescence from the tooth to which the dental plaque adhered and which was irradiated with light having the first wavelength, the intensity t2 of fluorescence from the clean tooth irradiated with light having the second wavelength, and the intensity t2' of fluorescence from the tooth to which the dental plaque adhered and which was irradiated with light having the second wavelength are listed in FIG. 11.

The substitutional value of the intensity t1' of the intrinsic fluorescence from the tooth was calculated based on t2'×t1/t2, and the amount Δp of the fluorescent substance originating from the dental plaque was determined by subtracting the substitutional value of the intensity t1' of the intrinsic fluorescence from the tooth from the intensity p1' of the fluorescence from the tooth to which the dental plaque adhered and which was irradiated with light having the first wavelength. As a result, the count number of the amount Δp was 1146.

In the experiment, LED currents were selected so that the intensities (corresponding to t1 in FIG. 1 and t2 in FIG. 2) of the intrinsic fluorescence at a wavelength of 638 nm from the tooth irradiated with light having the first wavelength and light having the second wavelength were approximately equal. However, purple light was found to be set at a level that is approximately 5.5% higher, as indicated by a value of the excitation light intensity ratio t1/t2 in FIG. 11 of 1.055. A difference between such intensities can be corrected by using the mathematical expression (3), even after measurement.

The above results revealed that measurement of fluorescence at one wavelength obtained by excitation of a tooth by light having two different wavelengths enables fluorescence originating from dental plaque to be separated from intrinsic fluorescence and to be measured, whereby a fluorescence measuring device capable of detecting dental plaque with high precision can be obtained. When the amount Δp of fluorescent substance originating from dental plaque is determined in such a manner and such a count number is almost zero, it is found that a tooth is in a clean state. Thus, one can brush one's teeth with a toothbrush including the fluorescence measuring device while numerically confirming whether the teeth are properly brushed.

Third Embodiment

In the optical measuring method described above, the teeth are irradiated with the excitation light having two wavelengths of 405 nm and 465 nm, and the amount of the dental plaque is determined based on the difference between the amounts of fluorescent substance in the examined light of the two wavelengths, on the assumption that the examined light detected in the irradiation with the excitation light at 465 nm does not include the fluorescence from the dental plaque. However, the fluorescence absorption peak of a fluorescent substance included in dental plaque is at around 400 nm, and absorbed fluorescence significantly decreases in a wavelength difference of around ±5 nm; in contrast, the fluorescence absorption peak of a tooth is very broad in comparison with the fluorescent substance included in the dental plaque, and can be regarded as approximately constant in a range of around ±5 nm. Therefore, the excitation light is not limited to excitation light at 405 nm and 465 nm, and a difference between the amounts of fluorescent substance due to dental plaque can be measured even when excitation light having two similar wavelengths between which the difference is around 5 nm, for example, is used. Thus, an optical measuring method in which excitation light having two wavelengths similar to each other is used will be described below.

Assuming that the amounts of fluorescent substance at around 635 nm generated by irradiating a tooth to which dental plaque adheres with excitation light having two similar wavelengths $\lambda 1$ and $\lambda 2$ (for example, $\lambda 1=400$ nm and $\lambda 2=405$ nm) are y1 and y2, respectively, the amounts of the fluorescent substance are expressed by the following mathematical expressions (4) and (5).

$$y1 = yt + p \times \eta 1 \quad (4)$$

$$y2 = yt + p \times \eta 2 \quad (5)$$

In the mathematical expressions, yt represents the amount of the fluorescent substance generated from the tooth, and p represents the amount of the dental plaque. $\eta 1$ and $\eta 2$ are constants representing the fluorescence efficiency of the fluorescent substance included in the dental plaque for the excitation light having the wavelengths $\lambda 1$ and $\lambda 2$, respectively.

When the amounts y1 and y2 of the fluorescent substance are obtained by measurement with the two wavelengths, the amount p of the dental plaque and the amount yt of the fluorescent substance generated by the tooth can be determined by the following mathematical expressions (7) and (8), on the assumption that the difference $\Delta \eta$ between $\eta 1$ and 2 is defined as the following mathematical expression (6), because $\eta 1$ and $\eta 2$ are the constants.

$$\Delta \eta = \eta 1 - \eta 2 \quad (6)$$

$$p = (p1 - p2)/\Delta \eta \quad (7)$$

$$yt = (y2 \times \eta 1 - y1 \times \eta 2)/\Delta \eta \quad (8)$$

In actual measurement, the losses of light occur in optical systems in an excitation side and a detection side, respectively. However, since the wavelength dependence of such losses can be corrected in advance and the wavelengths $\lambda 1$ and $\lambda 2$ of excitation light are similar, a difference between such losses due to the wavelengths may also be sufficiently reduced.

$\Delta \eta$ is a constant, and the inverse $1/\Delta \eta$ thereof corresponds to the sensitivity of detection of dental plaque. The value of the detection sensitivity may be experimentally determined and may be set at an optimal value. Alternatively, a sensitivity adjustment dial may be disposed in a fluorescence measuring device so that a user can adjust the value ($1/\Delta \eta$) of the detection sensitivity.

The entire configuration of a fluorescence measuring device in which the excitation light having the two similar wavelengths is used is similar to the entire configuration of the already described fluorescence measuring device 1 or 400. However, since the circuit configuration of the control unit 300 is different from the circuit configurations of the fluorescence measuring devices 1 and 400, a configuration example of the detection circuit of the control unit 300 in which excitation light having two similar wavelengths is used is described below.

Figure 12:
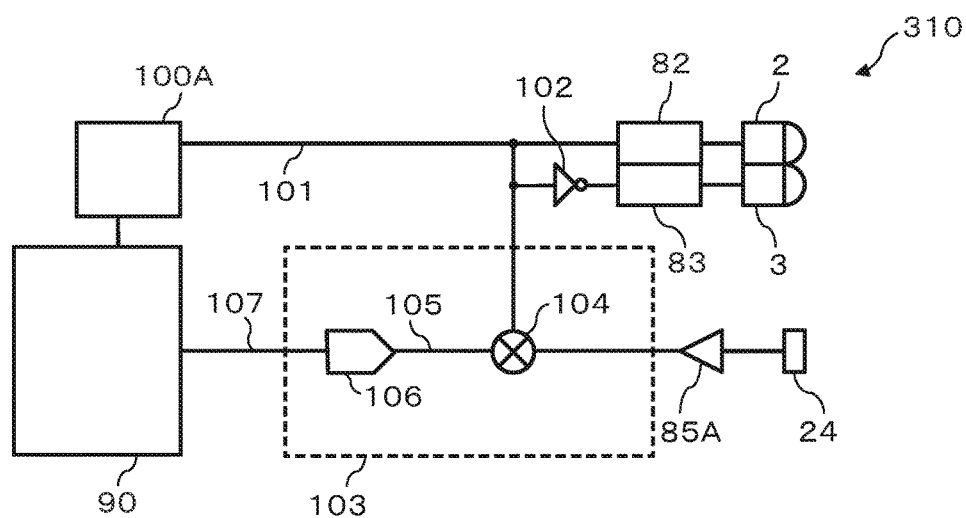
FIG. 12 is a view illustrating a configuration example of a detection circuit 310 using a lock-in amplifier.

FIG. 12 is a view illustrating a configuration example of a detection circuit 310 using a lock-in amplifier. An LED having a wavelength of 400 nm and an LED having a wavelength of 405 nm are used as a first light source 2 and a second light source 3, respectively. The respective LEDs are alternately driven by light source drive circuits 82 and 83 on the basis of a timing signal 101 from an oscillation circuit 100A. The first light source 2 is turned on in phase with the timing signal 101; and the second light source 3 is turned on in a phase opposite to the timing signal 101, since the second light source 3 is connected through an inverter 102.

Fluorescence generated on a tooth is detected by a light detector 24, and is converted into a voltage signal by a current-voltage conversion circuit 85A. Then, phase detection is performed in a lock-in amplifier 103 including a phase detector 104. As a result, a difference component between fluorescence generated in excitation light having a wavelength of 400 nm and fluorescence generated in excitation light having a wavelength of 405 nm is output as an in-phase detection output 105. The in-phase detection output 105 is converted into an in-phase detection digital output 107 by an A/D converter 106. Calculation of the digital signal is carried out by a control circuit 90, and the amount p of dental plaque in the mathematical expression (7) is calculated from fluorescence intensities.

Figure 13:
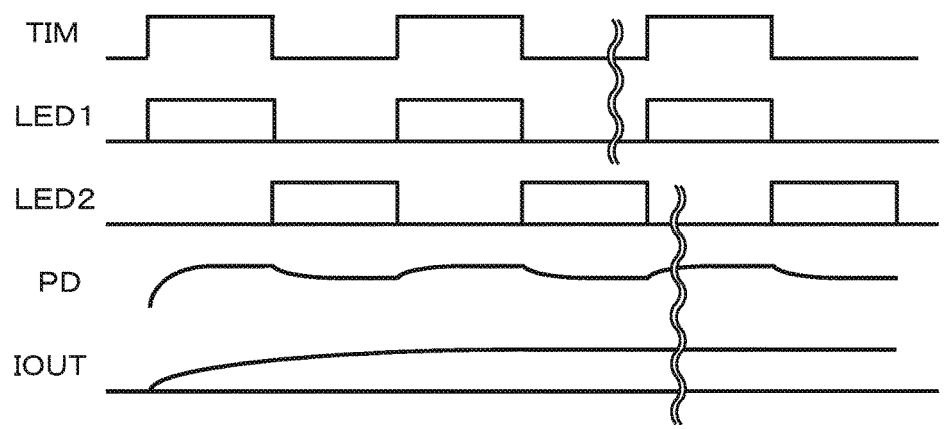
FIG. 13 is a timing chart indicating the timing of operation of the detection circuit 310.

FIG. 13 is a timing chart indicating the timing of operation of the detection circuit 310. In FIG. 13, the timing signal 101 is denoted by TIM, and the first light source 2 and the second light source 3 are denoted by LED1 and LED2, respectively. A light signal obtained after a photocurrent obtained in the light detector 24 has been converted into a voltage in the current-voltage conversion circuit 85A is denoted by PD, and the in-phase detection output 105 is denoted by IOUT.

The signal intensity of the light signal PD is increased in proportion to the fluorescence efficiency of dental plaque during a period in which LED1 is turned on, and is relatively lower during a period in which LED2 is turned on. The in-phase detection output 105 (IOUT) which is the difference component of fluorescence is obtained by phase detection of the light signal PD. The rising properties of IOUT are determined by the properties of a low-pass filter disposed in the phase detector 104.

Figure 14:
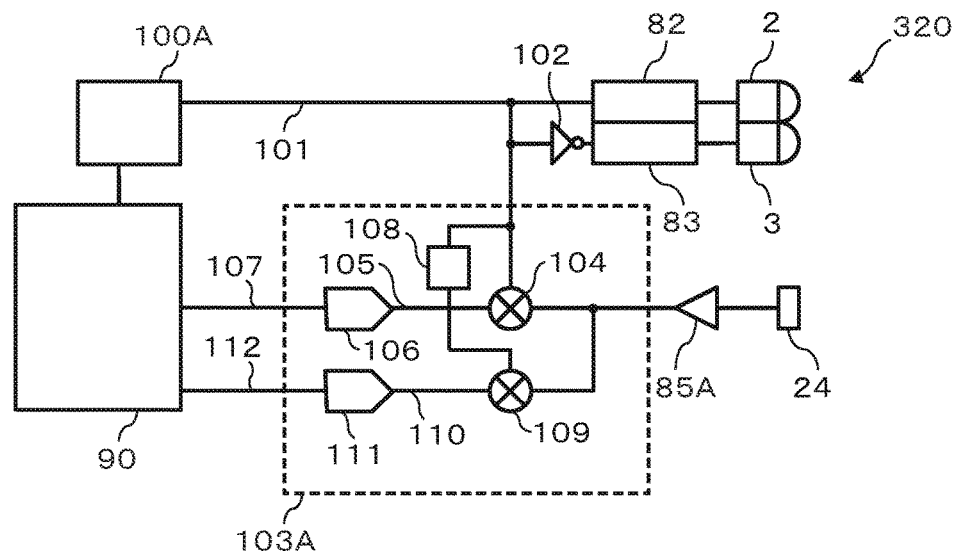
FIG. 14 is a view illustrating a configuration example of a detection circuit 320 using a two-phase lock-in amplifier.

FIG. 14 is a view illustrating a configuration example of a detection circuit 320 using a two-phase lock-in amplifier. The detection circuit 310 illustrated in FIG. 12 measures only the amount of dental plaque p, while the detection circuit 320 of FIG. 14 simultaneously detects the amount p of dental plaque and the amount yt of the fluorescent substance of a tooth using a lock-in amplifier 103A which operates in two phases. The detection circuit 320 differs from the detection circuit 310 in addition of a 90° phase shifter 108, a phase detector 109, and an A/D converter 111 to the lock-in amplifier 103A.

In the detection circuit 320, phase detection is carried out using a timing signal 101 and a signal obtained by delaying the timing signal 101 by the 90° phase shifter 108. An in-phase detection output 105 from a phase detector 104 is converted into an in-phase detection digital output 107 by an A/D converter 106, and a 90° phase detection output 110 from the phase detector 109 is converted into a 90° phase detection digital output 112 by the A/D converter 111. Calculation of such digital signals is carried out by a control circuit 90, and the amount p of dental plaque and the amount yt of the fluorescent substance of a tooth are calculated from fluorescence intensities on the basis of the mathematical expressions (7) and (8).

Figure 15:
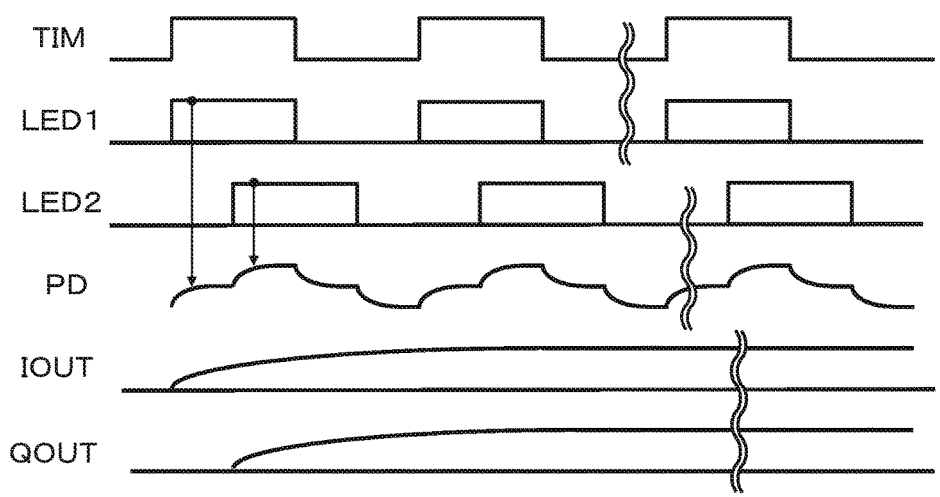
FIG. 15 is a timing chart indicating the timing of operation of the detection circuit 320.

FIG. 15 is a timing chart indicating the timing of operation of the detection circuit 320. Like FIG. 13, the timing signal 101, a first light source 2, a second light source 3, an output signal (light signal) from a current-voltage conversion circuit 85A, and the in-phase detection output 105 are denoted by TIM, LED1, LED2, PD, and IOUT, respectively. The 90° phase detection output 110 is denoted by QOUT.

In the detection circuit 320, LED2 is turned on with delay of a phase of 90° with respect to the timing of turning on LED1. In the light signal PD, fluorescence due to excitation light of LED1 is detected at a phase of 0°, and this fluorescence with fluorescence due to excitation light of LED2 superimposed thereon is detected at a phase of 90°, as indicated by the arrows in the figure. By phase detection of the light signal PD at 0° and 90°, the amount y1 of fluorescent substance due to excitation light of LED1 and the amount y2 of fluorescent substance are directly obtained as the in-phase detection output 105 (IOUT) and the 90° phase detection output 110 (QOUT), respectively. Accordingly, the amount p of dental plaque and the amount yt of the fluorescent substance of a tooth can be simultaneously measured using the mathematical expressions (7) and (8). Therefore, in the detection circuit 320, the distance between the tooth and a detection unit 200 can be corrected by normalization of the amount p of the dental plaque with the amount yt of the fluorescent substance of the tooth.

Alternatively, in the detection circuit 320, use of a drive waveform in which the first light source 2 and the second light source 3 (LED1 and LED2) are neither simultaneously turned on nor simultaneously turned off enables a change in the signal intensity of the light signal PD to be reduced to a low level, whereby the dynamic range of detection of the amount of fluorescent substance can be improved. Thus, the timing of operation of the detection circuit 320 in such a case will now be described.

Figure 16:
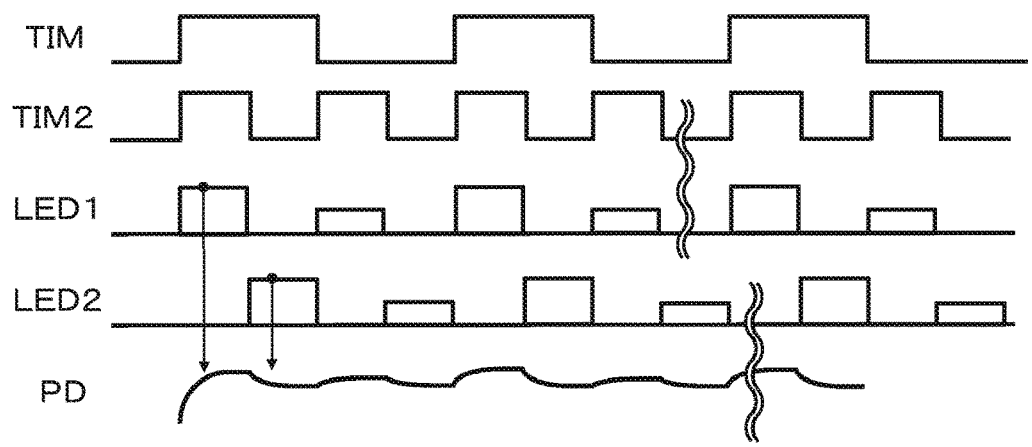
FIG. 16 is a timing chart indicating other timing of operation of the detection circuit 320.

FIG. 16 is a timing chart indicating other timing of operation of the detection circuit 320. Symbols TIM, LED1, LED2, and PD in the figure are the same as those in FIG. 15. In the example indicated in FIG. 16, LED1 and LED2 are alternately turned on by a timing signal TIM2 having a frequency two times the frequency of the timing signal 101 (TIM). TIM and TIM2 are used as phase signals for phase detection. Currents for driving LED1 and LED2 are modulated to a times (about 0.5 time in the illustrated example) in an interval in which TIM is L.

Assuming that the in-phase detection output 105 and the 90° phase detection output 110 are y1' and y2', respectively, y1' and y2' are obtained as the sum signal and difference signal of y1 and y2 as indicated in the following mathematical expressions (9) and (10).

$$y1'=(y1-y2)\times(1+\alpha) \tag{9}$$

$$y2'=(y1+y2)\times(1-\alpha) \tag{10}$$

Accordingly, y1 and y2 can be easily determined by calculation using the mathematical expressions (9) and (10). The sensitivity of detection of dental plaque is increased and the sensitivity of detection of a tooth is decreased by allowing α to approach 1, when the amount of fluorescent substance originating from the dental plaque is smaller than the amount of fluorescent substance generated by the tooth. As a result, a dynamic range can be improved.

It is preferable that the first wavelength of light emitted by the first light source 2 and the second wavelength of light emitted by the second light source 3 be, for example, in a range from 350 nm to 430 nm, and that the difference between the first wavelength and the second wavelength be 5 nm or more. However, measurement similar to the above-described measurement may be possible, when the difference between the first wavelength and the second wavelength is 1 nm or more, on the basis of the features of the fluorescence absorption peak of the fluorescent substance included in the dental plaque and the fluorescence absorption peak of the tooth. Therefore, the first wavelength and the second wavelength may be in a range from 350 nm to 430 nm, and the difference between the first wavelength and the second wavelength may be 1 nm or more. Use of wavelengths similar to each other as the first wavelength and the second wavelength as described above enables the wavelength dependence of the optical system and fluorescence from a tooth or dental plaque to be canceled with higher precision than use of two wavelengths, such as 405 nm and 465 nm, between which the difference is great, and therefore allows measurement precision to be improved.

Fourth Embodiment

In all of the optical measuring methods described above, a tooth is irradiated with excitation light having two wavelengths. However, the wavelengths of excitation light are not limited to two wavelengths and may be three or more wavelengths. Thus, an example in which a tooth is irradiated with excitation light having three wavelengths and the amount of dental plaque is measured is described below.

In the use of the excitation light having three wavelengths, the following mathematical expressions (11) to (13) corresponding to the mathematical expressions (4) and (5) described above are obtained.

$$y1=yt+p\times\eta1 \tag{11}$$

$$y2=yt+p\times\eta2 \tag{12}$$

$$y3=yt+p\times\eta3 \tag{13}$$

In the mathematical expressions, y1, y2, and y3 are the amounts of fluorescent substance at around 635 nm generated when a tooth to which dental plaque adheres is irradiated with the excitation light having wavelengths of λ1, λ2, and λ3, respectively. In addition, yt is the amount of fluorescent substance generated by the tooth, p is the amount of the dental plaque, and η1, η2, and η3 are the fluorescence efficiencies (constant) of the dental plaque for the excitation light having the wavelengths λ1, λ2, and λ3, respectively. In such a case, the amount p of the dental plaque can be determined by averaging values obtained from three combinations of two equations among the mathematical expressions (11) to (13).

Alternatively, the amounts y1, y2, and y3 of the fluorescent substance may be measured several times, and the estimated value of the amount p of the dental plaque may be calculated from measurement data sets of the amounts using a least square method as described below.

When the amount of the fluorescent substance is measured n times, n sets of data, in which each set includes three values of y1, y2, and y3, are obtained. For example, when i-th measurement data y1 is denoted by y1$i$ or the like, all the items of obtained data are represented by the following mathematical expressions (14).

$$y11 = yt + p \times \eta1$$
$$y21 = yt + p \times \eta2$$
$$y31 = yt + p \times \eta3$$
$$\ldots$$
$$y1n = yt + p \times \eta1$$
$$y2n = yt + p \times \eta2$$
$$y3n = yt + p \times \eta3$$

(14)

The mathematical expressions (14) are expressed in a vector form as the following mathematical expression (15).

$$Y = yt + pX \quad (15)$$

In the mathematical expression, Y is a vector including 3n components (y11, y21, y31, ...), and X is also a vector including 3n components ($\eta1$, $\eta2$, $\eta3$, ...). The amount p of the dental plaque can be calculated by a least square method using the mathematical expression (15) as an observation equation.

The entire configuration of a fluorescence measuring device in which the excitation light having the three wavelengths is used is similar to the entire configuration of the already described fluorescence measuring device 1 or 400. However, since the circuit configuration of the control unit 300 is different from the circuit configurations of the fluorescence measuring devices 1 and 400, a configuration example of the detection circuit of the control unit 300 in which excitation light having three similar wavelengths is used is described below.

Figure 17:
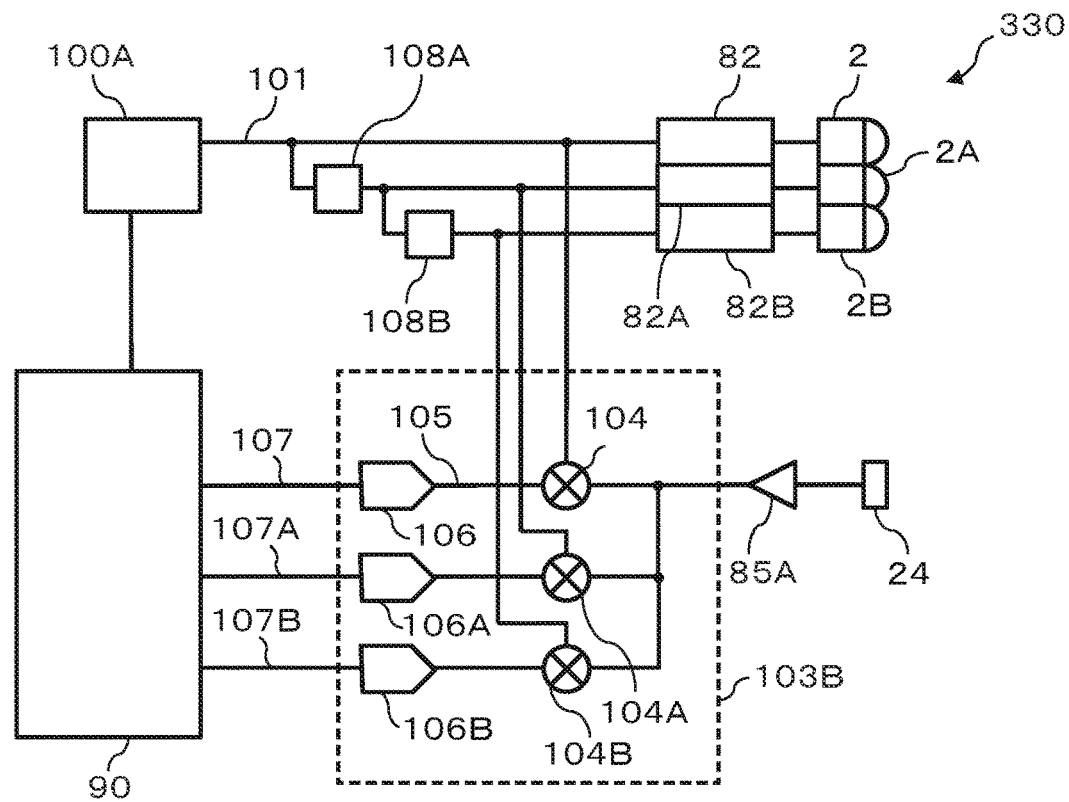
FIG. 17 is a view illustrating a configuration example of a detection circuit 330 in which excitation light having three wavelengths is used.
Figure 18:
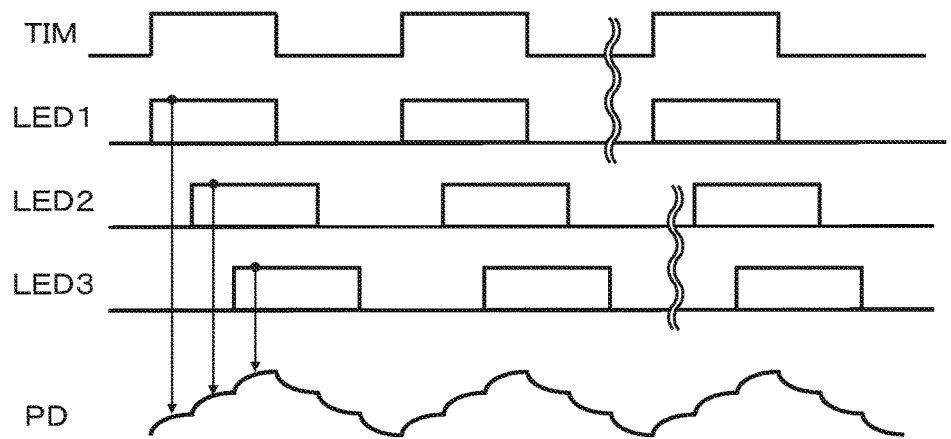
FIG. 18 is a timing chart indicating the timing of operation of the detection circuit 330.

FIG. 17 is a view illustrating a configuration example of a detection circuit 330 in which excitation light having three wavelengths is used. FIG. 18 is a timing chart indicating the timing of operation of the detection circuit 330. The detection circuit 330 is a detection circuit in which the detection circuit 320 of FIG. 14 is further generalized, and the number of the phases of the lock-in amplifier is increased to three.

The detection circuit 330 includes three light sources 2, 2A, and 2B that emit excitation light having wavelengths $\lambda1$, $\lambda2$, and $\lambda3$, respectively, and three light source drive circuits 82, 82A, and 82B that drive the respective light sources. Further, the detection circuit 330 includes three phase detectors 104, 104A, and 104B corresponding to the three wavelengths $\lambda1$, $\lambda2$, and $\lambda3$, as well as 60° phase shifters 108A and 108B. In the detection circuit 330, a timing signal 101 from an oscillation circuit 100A is used as an in-phase signal, and phase signals of 60° and 120° are generated by the 60° phase shifters 108A and 108B. An example in which the phase signals which are not orthogonal to each other are used is described here in order to simplify the circuit, although phase signals orthogonal to each other are used in ordinary phase detection.

Output signals from the phase detectors 104, 104A, and 104B are converted into digital detection signals 107, 107A, and 107B by A/D converters 106, 106A, and 106B, respectively. Since detected fluorescence due to the excitation light having the three wavelengths $\lambda1$, $\lambda2$, and $\lambda3$ are mixed in the detection signals 107, 107A, and 107B, the amount of fluorescent substance corresponding to each wavelength is separated by calculation in a control circuit 90 as described below.

Assuming that phase detection outputs (detection signals 107, 107A, and 107B) in three phases are y1', y2', and y3', respectively, the amounts y1, y2, and y3 of fluorescent substance due to the excitation light having the three wavelengths $\lambda1$, $\lambda2$, and $\lambda3$ are mixed in a manner as represented in the following mathematical expressions (16) to (18).

$$y1' = (3y1 + y2 - y3)/3 \quad (16)$$
$$y2' = (y1 + 3y2 + y3)/3 \quad (17)$$
$$y3' = (-y1 + y2 + 3y3)/3 \quad (18)$$

The simultaneous equations can be solved for y1, y2, and y3 as represented in the following mathematical expressions (19) to (21).

$$y1 = (2y1' - y2' + y3') \times \tfrac{3}{4} \quad (19)$$
$$y2 = (-y1' + 2y2' - y3') \times \tfrac{3}{4} \quad (20)$$
$$y3 = (y1' - y2' + 2y3') \times \tfrac{3}{4} \quad (21)$$

Accordingly, the control circuit 90 determines the amounts y1, y2, and y3 of fluorescent substance corresponding to the wavelengths $\lambda1$, $\lambda2$, and $\lambda3$, respectively, according to the mathematical expressions (19) to (21).

It is assumed that the amount yt of fluorescent substance generated from a tooth is constant in the above calculation. However, the amount of dental plaque can also be determined as follows, in consideration of a difference between fluorescence efficiencies due to the wavelengths of excitation light.

Assuming that the amount of fluorescent substance causing fluorescence to be generated from a tooth is q and the fluorescence efficiencies according to the wavelengths are $\eta t1$, $\eta t2$, and $\eta t3$, the amounts y1, y2, and y3 of fluorescent substance are represented by the following mathematical expressions (22) to (24).

$$y1 = q \times \eta t1 + p \times \eta1 \quad (22)$$
$$y2 = q \times \eta t2 + p \times \eta2 \quad (23)$$
$$y3 = q \times \eta t3 + p \times \eta3 \quad (24)$$

The amount q of fluorescent substance and the amount p of dental plaque can be simultaneously determined from n sets of data in the same manner as described above, by defining an observation equation as the following mathematical expression (25) in which Z is a vector including 3n components ($\eta t1$, $\eta t2$, $\eta t3$, ...), according to the calculation method by the least square method described above.

$$Y = qZ + pX \quad (25)$$

An optical measuring method using excitation light having three wavelengths is insusceptible to noise such as environmental light. This is because only a component in which the amount of fluorescent substance desirably varies can be detected, in a reflection of a variation in fluorescence efficiency due to the wavelengths. The probability that signal intensity desirably varies due to noise by accident is decreased with increasing the complexity of wavelengths (fluorescence efficiencies) and the order thereof. Accordingly, with increasing the number of wavelengths, resistance to noise is enhanced, and an improvement of S/N ratio and enhancement of sensitivity can be expected.

Although not illustrated, even when excitation light having three wavelengths is used, the dynamic range of detection of the amount of fluorescent substance can be similarly improved by using a drive waveform in which light sources are neither simultaneously turned on nor simultaneously turned off, as the operation timing indicated in FIG. 16.

Fifth Embodiment

When the amount of dental plaque is fed back to a user in real time by sound or vibrations during toothbrushing, usability may be improved by feeding back, at the time of touching a tooth with the leading ends of the brushes, the amount of dental plaque on the touched location. For such a purpose, a method is suitable in which the same optical waveguide is used in common as the optical waveguide 6 for emitting light and the optical waveguide 22 for receiving light in the fluorescence measuring device 1 or 400 described above, and thereby the emission unit and the light-receiving unit are allowed to be the same. Thus, a fluorescence measuring device in which the same optical waveguide is disposed as the optical waveguide 6 for emitting light and the optical waveguide 22 for receiving light is described below.

Figure 19:
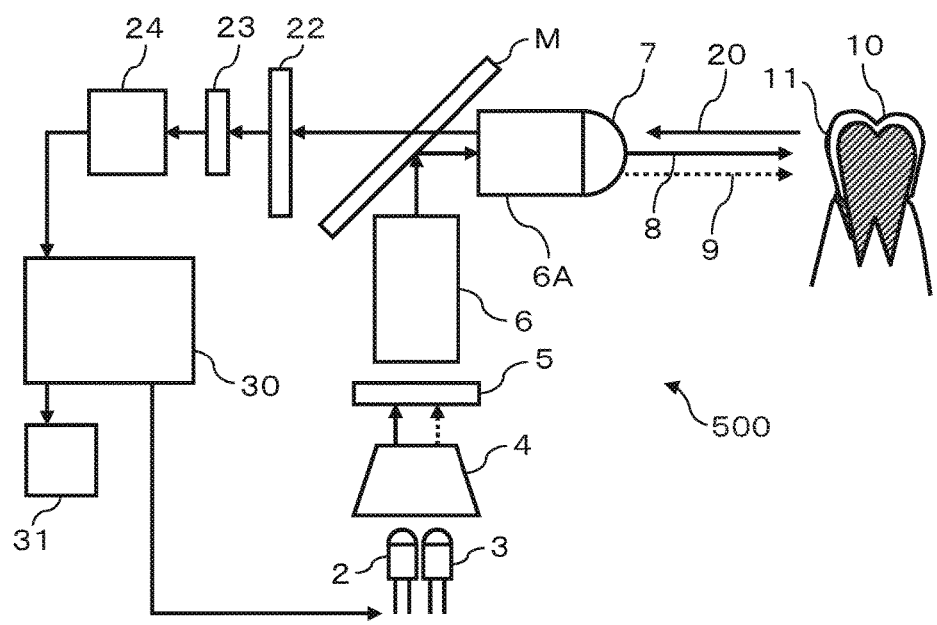
FIG. 19 is a configuration view of another fluorescence measuring device 500.

FIG. 19 is a configuration view of another fluorescence measuring device 500. Components common to the components of the fluorescence measuring device 1 or 400 described above are denoted by the same reference characters as those of the fluorescence measuring devices, and the overlapping description thereof is omitted. In the fluorescence measuring device 500, a shared optical waveguide 6A is used as an optical waveguide for emitting light and an optical waveguide for receiving light in common.

In the fluorescence measuring device 500, excitation light from a first light source 2 or a second light source 3 is incident on a mirror M through a color mixture unit 4, an optical filter 5 for emitting light, and an optical waveguide 6 for emitting light. The mirror M includes a dichroic mirror, a half mirror, or the like, and has the properties of reflecting light in the wavelength region of excitation light and transmitting light in the wavelength region of fluorescence. Accordingly, excitation light from the first light source 2 or the second light source 3 is reflected by the mirror M, and passes through the shared optical waveguide 6A, and a tooth 10 including a portion 11 to which dental plaque adheres is irradiated with the excitation light as first irradiation light 8 or second irradiation light 9 from a light condensation unit 7 for emitting light. Examined light 20 (fluorescence) from the tooth 10 is incident on the light condensation unit for emitting light, re-passes through the shared optical waveguide 6A, and arrives at the mirror M. However, since the mirror M transmits light in the wavelength region of fluorescence, the examined light 20 passes through the mirror M and arrives at a light detector 24 through an optical waveguide 22 for receiving light and an optical filter 23 for receiving light.

In the fluorescence measuring device 500, the optical filter 5 for emitting light and the optical filter 23 for receiving light can be omitted.

For example, one brush of a toothbrush can be used as the shared optical waveguide 6A in the fluorescence measuring device 500. In such a case, dental plaque can be stably detected because emitted light is not shielded by a brush other than brushes for receiving light. Accordingly, detection can be reliably performed particularly in a gap portion such as an interdental space or a periodontal pocket, to which dental plaque easily adheres, and practical usefulness is therefore provided.

Sixth Embodiment

In all the optical measuring methods described above, fluorescence is detected as examined light from a tooth. However, the amount of dental plaque can also be measured by detecting a change in the intensity of the reflected light of excitation light with which a tooth has been irradiated. Thus, an optical measuring method in which reflected light of excitation light is used as examined light is described below.

Figure 20:
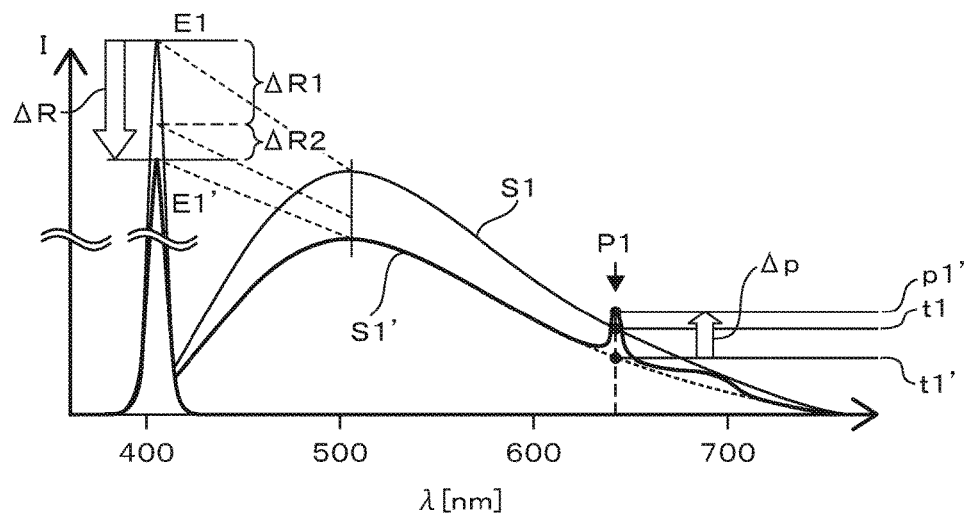
FIG. 20 is a graph illustrating the spectra of reflected light and fluorescence obtained by irradiating a tooth to which dental plaque adheres and a clean tooth with excitation light at 405 nm.
Figure 21:
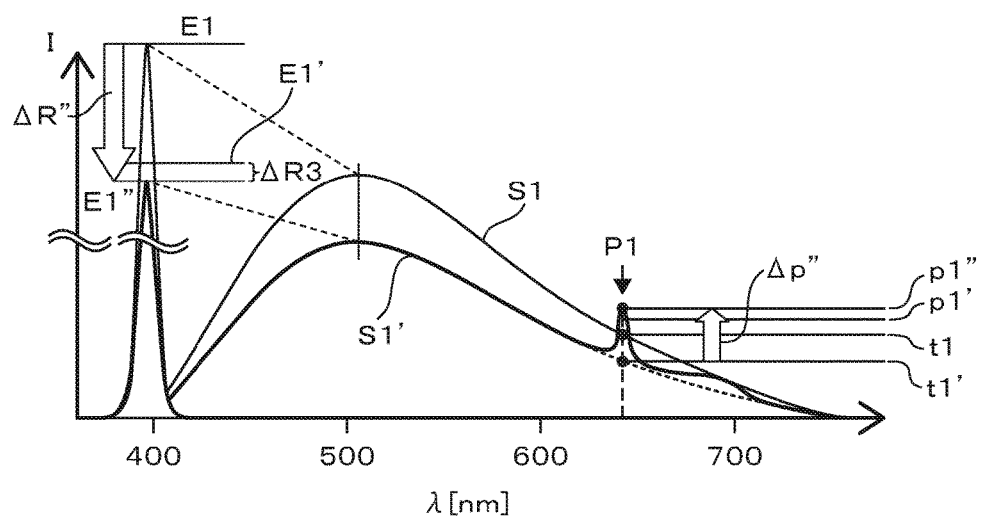
FIG. 21 is a graph illustrating the spectra of reflected light and fluorescence obtained by irradiating the tooth to which the dental plaque adheres and the clean tooth with excitation light at 400 nm.

FIG. 20 is a graph illustrating the spectra of reflected light and fluorescence obtained by irradiating a tooth to which dental plaque adheres and a clean tooth with excitation light at 405 nm. FIG. 21 is a graph illustrating the spectra of reflected light and fluorescence obtained by irradiating the tooth to which the dental plaque adheres and the clean tooth with excitation light at 400 nm. The horizontal axis of each graph indicates a wavelength $\lambda$ (nm), and the vertical axis of each graph indicates the intensity I of fluorescence or reflected light. Like FIG. 1 and FIG. 2, the thin line of each graph represents the spectrum S1 obtained from the clean tooth, and the thick line of each graph represents the spectrum S1' obtained from the tooth to which the dental plaque adheres.

First, the spectra S1' are observed with attention to fluorescence at 635 nm indicated by P1 in the figures. The amount $\Delta p''$ of fluorescent substance originating from the dental plaque in excitation of the tooth to which the dental plaque adheres at a wavelength of 400 nm is larger than the amount $\Delta p$ of fluorescent substance originating from the dental plaque in excitation of the same tooth at a wavelength of 405 nm, because the fluorescence efficiency of the fluorescent substance included in the dental plaque is high. In other words, the intensity of fluorescence having a wavelength of 635 nm corresponds to the sum of the amount t1' of the fluorescent substance of the tooth and the amount $\Delta p$ of the fluorescent substance of the dental plaque in the excitation at a wavelength of 405 nm, and corresponds to the sum of the amount t1' of the fluorescent substance of the tooth and the amount $\Delta p''$ ($>\Delta p$) of the fluorescent substance of the dental plaque in the excitation at a wavelength of 400 nm.

Then, the spectra are observed with attention to reflected light. The intensity E1' of reflected light in excitation of the tooth to which the dental plaque adheres at a wavelength of 405 nm is less than the intensity E1 of reflected light in excitation of the clean tooth at a wavelength of 405 nm for the following two reasons. The first reason is that a decrease $\Delta R1$ occurs due to scattering on the dental plaque because the dental plaque itself has the property of scattering light. The second reason is that a decrease $\Delta R2$ occurs due to the absorption of fluorescence by the fluorescent substance included in the dental plaque. Because part of light energy absorbed by the fluorescent substance included in the tooth is released as fluorescence at a wavelength of around 635 nm, the decrease $\Delta R2$ is proportional to the amount $\Delta p$ of the fluorescent substance.

The intensity of the reflected light at a wavelength of 405 nm corresponds to the sum of a decrease due to scattering on the dental plaque and a decrease due to the absorption of fluorescence by the dental plaque. With regard to the sum, $\Delta R''$ in the excitation at a wavelength of 400 nm is larger than $\Delta R$ in the excitation at a wavelength of 405 nm, because the absorption of fluorescence by the dental plaque increases as indicated by symbol $\Delta R3$ in FIG. 21. Accordingly, the amount of the dental plaque can be estimated from the ratio or difference between the intensities of light reflected when the tooth is irradiated with the excitation light having the wavelengths different from each other.

With attention to the fact that a decrease in the intensity of reflected light represents an increase in the amount of dental plaque, a specific calculation method in which reflected light is used as examined light is fundamentally the same as the calculation method in which fluorescence is used as examined light, except that the directions of variations (increase and decrease) are opposite to each other.

The entire configuration of an optical measuring device (reflected-light measuring device) in which reflected light is used as examined light is similar to the entire configuration of the already described fluorescence measuring device 1, 400, or 500. However, the optical filter 5 for emitting light is not necessary in the reflected-light measuring device, because it is not needed to cut a frequency region corresponding to a fluorescence region. In the reflected-light measuring device, an optical filter that cuts 430 nm or more is preferably used as the optical filter 23 for receiving light.

The invention claimed is:

1. An optical measuring device detecting fluorescence of a substance to be measured, the substance adhering to a sample emitting intrinsic fluorescence, the optical measuring device comprising:
   first and second light sources that respectively emit first light and second light exciting the sample, the second light having a longer wavelength and lower excitation efficiency for the substance than the first light;
   an optical filter on which the fluorescence is incident, the optical filter substantially transmitting only light in a wavelength region including a peak wavelength of the fluorescence of the substance, wherein the light in the wavelength region is such that first intensity of fluorescence generated by the first light is different from second intensity generated by the second light,
   a detection unit that detects light transmitted through the optical filter,
   a control unit that calculates a ratio or difference between the first intensity of fluorescence detected when the sample is irradiated with the first light and second intensity of fluorescence detected when the sample is irradiated with the second light,
   thereby obtaining an intensity of fluorescence without the intrinsic fluorescence, to calculate the amount of fluorescence of the substance.

2. The optical measuring device according to claim 1, wherein the sample is irradiated alternately with the first light and the second light.

3. The optical measuring device according to claim 1, wherein the first light has a wavelength in a range from 350 nm to 430 nm, and the second light has a wavelength in a range from 435 nm to 500 nm.

4. The optical measuring device according to claim 1, wherein the first light and the second light have wavelengths in a range from 350 nm to 430 nm, and
   a difference between the wavelengths is 5 nm or more.

5. The optical measuring device according to claim 1, further comprising a color mixture unit that makes intensity distributions uniform in a surface irradiated with the light emitted from the first light source and the second light source.

6. The optical measuring device according to claim 1, further comprising a second optical filter on which the first light and the second light are incident, wherein the second optical filter transmits only light in a wavelength region of the first light source and the second light source.

7. The optical measuring device according to claim 1, wherein
   the first and second light sources comprise an optical waveguide for emitting light, through which the first light and the second light are guided,
   the detection unit comprises an optical waveguide for receiving light, through which the fluorescence emitted by the substance is guided, and
   the optical waveguide for emitting light and the optical waveguide for receiving light are formed by a same optical waveguide.

8. The optical measuring device according to claim 1, wherein the sample is a tooth, and the substance is protoporphyrin IX included in dental plaque.

9. The optical measuring device according to claim 8, wherein the first intensity and the second intensity are intensities of fluorescence at a wavelength corresponding to a peak at around 635 nm in a spectrum of fluorescence of the dental plaque.

10. The optical measuring device according to claim 1, wherein
    turning on the first light source, turning on the second light source, and turning off both the first light source and the second light source are repeated,
    the detection unit further detects an intensity of environmental light when both the first light source and the second light source are turned off, and
    the control unit calculates the amount of the fluorescent substance, based on a difference between the first intensity and the intensity of environmental light, and a difference between the second intensity and the intensity of environmental light.

11. The optical measuring device according to claim 1, wherein
    the first light source is turned on in phase with a timing signal,
    the second light source is turned on in a phase opposite to the timing signal, and
    the control unit includes
    a phase detector that performs phase detection using the timing signal and thereby outputs a difference between the first intensity and the second intensity, and
    a control circuit that calculates the amount of fluorescence of the substance from the difference.

12. The optical measuring device according to claim 1, wherein
    the first light source is turned on in phase with a timing signal,
    the second light source is turned on with delay of a predetermined phase with respect to timing of turning on the first light source, and
    the control unit includes
    a first phase detector that performs phase detection using the timing signal and thereby generates a first output signal according to the first intensity and the second intensity,
    a second phase detector that performs phase detection using a signal obtained by delaying the timing signal and thereby generates a second output signal according to the first intensity and the second intensity, and
    a control circuit that calculates the amount of the fluorescent substance to be measured and an amount of a fluorescent substance of the sample, from the first output signal and the second output signal.

13. The optical measuring device according to claim 12, wherein
    the first light source and the second light source are light-emitting diodes, and are alternately turned on in accordance with a second timing signal having a frequency twice as large as the timing signal, and
    currents for driving the light-emitting diodes are decreased by a factor of a predetermined constant in intervals where the timing signal is low, as compared to the currents in intervals where the timing signal is high.

14. A toothbrush comprising the optical measuring device according to claim 1.

* * * * *